United States Patent
Risser et al.

(10) Patent No.: US 10,018,853 B2
(45) Date of Patent: *Jul. 10, 2018

(54) METHODS OF ALTERING THE REFRACTIVE INDEX OF MATERIALS

(71) Applicant: Battelle Memorial Institute, Columbus, OH (US)

(72) Inventors: Steven M. Risser, Reynoldsburg, OH (US); Vincent D. McGinniss, Columbus, OH (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 29 days.

This patent is subject to a terminal disclaimer.

(21) Appl. No.: 15/068,377

(22) Filed: Mar. 11, 2016

(65) Prior Publication Data

US 2016/0195734 A1 Jul. 7, 2016

Related U.S. Application Data

(60) Continuation of application No. PCT/US2014/054949, filed on Sep. 10, 2014, and a continuation-in-part of application No. 13/537,939, filed on Jun. 29, 2012, now Pat. No. 9,421,090, which is a division of application No. 12/936,005, filed as application No. PCT/US2009/039409 on Apr. 3, 2009, now Pat. No. 9,232,993.

(60) Provisional application No. 61/876,909, filed on Sep. 12, 2013, provisional application No. 61/090,339, filed on Aug. 20, 2008, provisional application No. 61/042,293, filed on Apr. 4, 2008.

(51) Int. Cl.
| | |
|---|---|
| G02C 7/04 | (2006.01) |
| G02C 7/02 | (2006.01) |
| A61L 27/50 | (2006.01) |
| G02B 1/04 | (2006.01) |
| A61F 2/16 | (2006.01) |

(52) U.S. Cl.
CPC .............. *G02C 7/022* (2013.01); *A61L 27/50* (2013.01); *G02C 7/04* (2013.01); *A61F 2/1627* (2013.01); *A61F 2/1635* (2013.01); *A61F 2/1659* (2013.01); *A61F 2002/16965* (2015.04); *A61L 2430/16* (2013.01); *G02B 1/043* (2013.01)

(58) Field of Classification Search
CPC ..................................................... G02B 1/043
See application file for complete search history.

(56) References Cited

U.S. PATENT DOCUMENTS

| | | |
|---|---|---|
| 785,075 A | 3/1905 | Anderson |
| 4,085,165 A | 4/1978 | Odaka et al. |
| 4,387,215 A | 6/1983 | Bailey |
| 4,390,676 A | 6/1983 | Loshaek |
| 4,528,311 A | 7/1985 | Beard et al. |
| 4,571,377 A * | 2/1986 | McGinniss ............ G03F 7/031 430/281.1 |
| 4,929,250 A | 5/1990 | Hung et al. |
| 4,954,132 A | 9/1990 | Hung et al. |
| 5,266,077 A | 11/1993 | Auten et al. |
| 5,352,245 A | 10/1994 | Su et al. |
| 5,662,707 A | 9/1997 | Jinkerson |
| 6,086,204 A | 7/2000 | Magnante |
| 6,187,042 B1 | 2/2001 | Sheets, Jr. et al. |
| 6,305,802 B1 | 10/2001 | Roffman et al. |
| 6,391,983 B1 | 5/2002 | Bateman et al. |
| 6,458,865 B2 | 10/2002 | Chappelow et al. |
| 7,052,133 B2 | 5/2006 | Lindacher et al. |
| 7,074,840 B2 | 6/2006 | Chang et al. |
| 7,134,755 B2 | 11/2006 | Jethmalani et al. |
| 7,249,847 B2 | 7/2007 | Dreher |
| 7,566,745 B2 | 7/2009 | Kawaguchi et al. |
| 7,744,785 B2 | 6/2010 | Phelan |
| 7,762,667 B2 | 7/2010 | Andino et al. |
| 7,780,293 B2 | 8/2010 | Andino et al. |
| 7,860,594 B2 | 12/2010 | Andino et al. |
| 7,905,594 B2 | 3/2011 | Widman et al. |
| 7,927,519 B2 | 4/2011 | Domschke et al. |
| 8,109,999 B2 * | 2/2012 | Hampp ................. A61F 2/1613 623/6.56 |
| 9,232,993 B2 * | 1/2016 | McGinniss ........... A61F 2/1627 |
| 2002/0022008 A1 | 2/2002 | Forest et al. |
| 2002/0025999 A1 | 2/2002 | Shakhnovich |
| 2002/0169201 A1 | 11/2002 | Falchuk |
| 2002/0196409 A1 | 12/2002 | Jani |

(Continued)

FOREIGN PATENT DOCUMENTS

| | | |
|---|---|---|
| DE | 10 2005 045540 A1 | 3/2007 |
| EP | 2290408 A1 | 8/2010 |

(Continued)

OTHER PUBLICATIONS

International Search Report and Written Opinion dated Dec. 8, 2014 and issued in PCT/US2014/054949.

(Continued)

Primary Examiner — Michael Pepitone
(74) Attorney, Agent, or Firm — Fay Sharpe LLP

(57) ABSTRACT

Methods and devices for altering the power of a lens, such as an intraocular lens, are disclosed. In one method, the lens comprises a single polymer matrix containing crosslinkable pendant groups, wherein the polymer matrix increases in volume when crosslinked. The lens does not contain free monomer. Upon exposure to ultraviolet radiation, crosslinking causes the exposed portion of the lens to increase in volume, causing an increase in the refractive index. In another method, the lens comprises a polymer matrix containing photobleachable chromophores. Upon exposure to ultraviolet radiation, photobleaching causes a decrease in refractive index in the exposed portion without any change in lens thickness. These methods avoid the need to wait for diffusion to occur to change the lens shape and avoid the need for a second exposure to radiation to lock in the changes to the lens.

8 Claims, 13 Drawing Sheets

(56) References Cited

U.S. PATENT DOCUMENTS

| | | |
|---|---|---|
| 2003/0022105 A1 | 1/2003 | Prasad et al. |
| 2005/0195361 A1 | 9/2005 | Jethmalani et al. |
| 2005/0283234 A1 | 12/2005 | Zhou et al. |
| 2006/0106262 A1 | 5/2006 | McGinniss et al. |
| 2006/0115516 A1 | 6/2006 | Pearson et al. |
| 2007/0055369 A1 | 3/2007 | Grubbs et al. |
| 2007/0076167 A1 | 4/2007 | Kumar et al. |
| 2007/0100018 A1 | 5/2007 | Hagting et al. |
| 2008/0027537 A1 | 1/2008 | Gerlach et al. |
| 2009/0157178 A1 | 6/2009 | Hampp |
| 2009/0248150 A1 | 10/2009 | Lehman |
| 2009/0287306 A1 | 11/2009 | Smith et al. |
| 2010/0318185 A1 | 12/2010 | Nunez et al. |

FOREIGN PATENT DOCUMENTS

| | | | |
|---|---|---|---|
| JP | 59087 126 A | 5/1984 | |
| WO | WO 00/41650 A1 | 7/2000 | |
| WO | WO 01/05578 | 1/2001 | |
| WO | WO 02/22004 | 3/2002 | |
| WO | WO 2004/015481 | 2/2004 | |
| WO | WO 2007033831 A1 * | 3/2007 | ........... A61F 2/1613 |
| WO | WO 2008021349 A1 * | 2/2008 | ........... A61L 12/086 |
| WO | WO 2008/134555 | 11/2008 | |
| WO | WO 2009124231 A1 | 10/2009 | |

OTHER PUBLICATIONS

Bailey, W.J.; Cationic Polymerization with Expansion in Volume; J. Macromol. Sci. Chem.; A9 (5); pp. 849-865; 1975.

Bailey, W.J.; Matrices that Expand on Curing for High Strength Composites and Adhesives; Materials Science and Engineering; A126; pp. 271-279; 1990.

Byerley et al.; Synthesis and polymerization of new expanding dental monomers; Dental Materials; vol. 8; pp. 345-350; Nov. 1992.

Moszner et al.; New developments of polymeric dental composites; Prog. Polym. Sci.; vol. 26; pp. 535-576; 2001.

International Search Report and Written Opinion of International Application No. PCT/US2009/039409, dated Jun. 4, 2009.

Supplementary European Search Report for Application No./Patent No. 09726752.0-1455 / 2268230 PCT/US2009/039409; Date of completion of the search: Feb. 13, 2013; Place of search: The Hague.

European Search Report and European Search Opinion of European Application No. EP 12007086, dated Jun. 20, 2013.

* cited by examiner

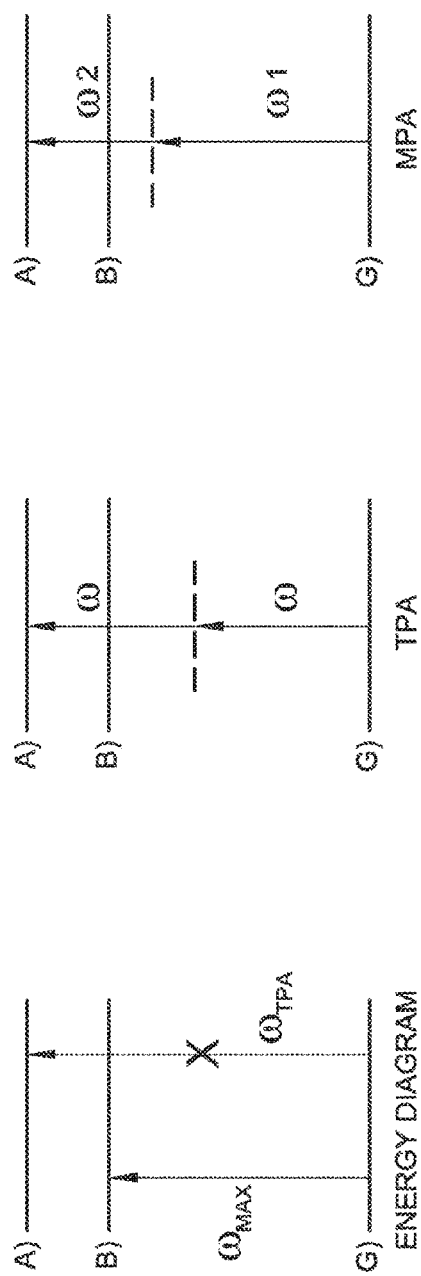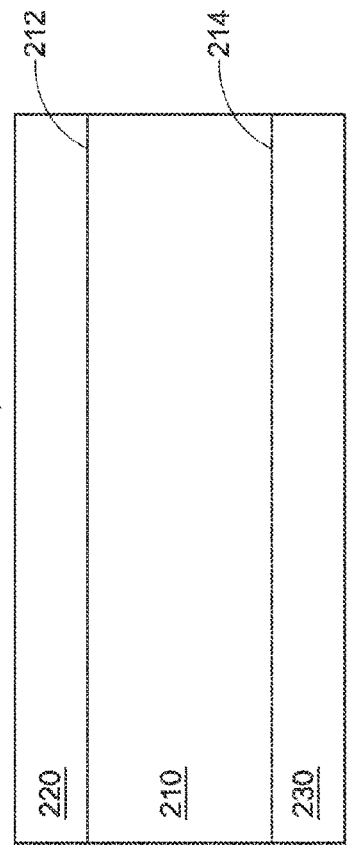

METHODS OF ALTERING THE REFRACTIVE INDEX OF MATERIALS

CROSS-REFERENCE TO RELATED APPLICATIONS

This application is a continuation of PCT Patent Application No. PCT/US2014/054949, filed Sep. 10, 2014, which claims priority to U.S. Provisional Patent Application Ser. No. 61/876,909, filed on Sep. 12, 2013. That application is hereby fully incorporated by reference herein. This application is also a continuation-in-part of U.S. patent application Ser. No. 13/537,939, filed Jun. 29, 2012, which is a divisional of U.S. patent application Ser. No. 12/936,005, filed Feb. 28, 2011, now U.S. Pat. No. 9,232,993, issued Jan. 12, 2016, which is a 371 of PCT Patent Application No. PCT/US2009/039409, filed Apr. 3, 2009, which claimed priority to U.S. Provisional Patent Application Ser. No. 61/090,339, filed Aug. 20, 2008, and to U.S. Provisional Patent Application Ser. No. 61/042,293, filed Apr. 4, 2008.

BACKGROUND

The present disclosure relates to methods and devices that are useful for adjusting the optical power of a lens. Such optical lenses may include lenses in eyewear that are exterior to the eye and ophthalmic lenses that are used in close proximity to the eye.

The eye can suffer from several different defects that affect vision. Common defects include myopia (i.e. near-sightedness) and hyperopia (i.e farsightedness). These types of defects occur when light does not focus directly on the retina, and can be corrected by the use of corrective lenses, such as eyeglasses or contact lenses.

In particular, the lens of the eye is used to focus light on the retina. The lens is usually clear, but can become opaque (i.e. develop a cataract) due to age or certain diseases. The usual treatment in this case is to surgically remove the opaque lens and replace it with an artificial or intraocular lens.

It can be desirable to be able to adjust such lenses, either before they are provided to a user or afterwards. In the case of eyeglasses and/or contact lenses, this permits the economical manufacture of lenses which can then be custom-fitted or adjusted to correct manufacturing defects. Such adjustments can also be useful in correcting misplacement of an intraocular lens during the surgical operation and/or to treat higher order optical aberrations. A common method is to use ultraviolet (UV) activation to induce the change in lens performance, to allow for high spatial resolution of the adjustment (due to the low wavelength of UV). After the lens is adjusted, the lens should not appreciably change in performance over the lifetime of the lens.

U.S. Pat. No. 7,134,755 describes a lens that uses ultraviolet light curable monomers in a silicone polymer matrix. The monomers are selectively polymerized using a digital light delivery system to alter the lens power at specific points.

There are two distinct effects that alter the lens optical power in this system. First, the polymerization of the UV curable monomers changes the refractive index of the system from n=1.4144 to n=1.4229, which would increase the optical power of the test lens from 95.1 diopters to 96.7 diopters. This change in the lens power is much smaller than the change in lens power that was reported in the patent, indicating this is not the primary mechanism of index change in this patent.

The second effect, which is responsible for the largest component of the change in lens optical power, is a swelling of the lens in the irradiated region. This swelling effect is illustrated in FIG. 1.

In FIG. 1A, free monomers (denoted M) are present in a silicone polymer matrix 10. In FIG. 1B, a mask 20 is used to expose only a portion 30 of the lens to UV radiation. The monomers in the region exposed to the UV radiation undergo polymerization, forming polymers P and slightly changing the refractive index. Over time, as seen in FIG. 1C, monomers from the un-exposed regions 40, 50 then migrate into the exposed region 30, causing that region to swell. This change in the lens thickness then leads to a larger change in the optical power. In FIG. 1D, after the migration of the monomer is finished, the whole lens is then exposed to UV radiation to freeze the changes.

There are several shortcomings to this method. One is that the primary change in the lens optical power is due to diffusion of monomer, which is a relatively slow process. Another shortcoming is that the dependence on diffusion as the operative effect limits the spatial resolution of the changes in the lens optical power. A third shortcoming is that the increase in lens thickness in the exposed region forces a thickness decrease in adjacent regions, as monomer from the adjacent region diffuses into the exposed region. This change in thickness in the adjacent regions is not easily controllable. Lenses without these shortcomings and others are desirable.

BRIEF DESCRIPTION

Disclosed in various embodiments are devices and methods for adjusting the optical power of a lens. Among other benefits, these lenses do not contain free monomers, so there is no change in lens shape due to diffusion of monomers. There is also no need for a second UV radiation exposure of the total lens to "lock-in" the refractive index changes.

Disclosed in some embodiments is a lens comprising: a single polymer matrix having crosslinkable pendant groups, wherein the polymer matrix increases in volume when crosslinked; and wherein substantially no free monomers are present therein.

The lens may further comprise a UV absorbing layer on at least one surface of the lens.

The pendant group may be 3,9-divinyl-2,4,8,10-tetraoxy-spiro[5.5]undecane.

Disclosed in other embodiments is a lens comprising a polymer matrix including photobleachable chromophores.

The photobleachable chromophores may be dispersed within the polymer matrix, or be present as pendant groups on the polymer matrix.

At least one chromophore may comprise a reactive site which can crosslink with a reactive site on the polymer matrix.

The photobleachable chromophores may comprise chromophores containing a malononitrile moiety, such as those of Formula (I) or Formula (II):

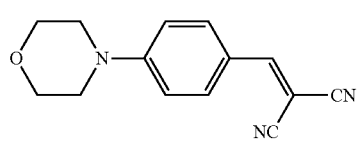

Formula (I)

-continued

Formula (II)

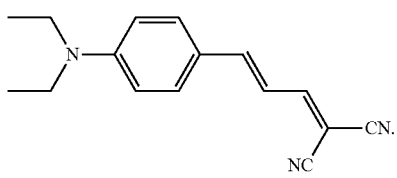

Alternatively, the photobleachable chromophores may comprise stilbene chromophores of Formula (III):

Formula (III)

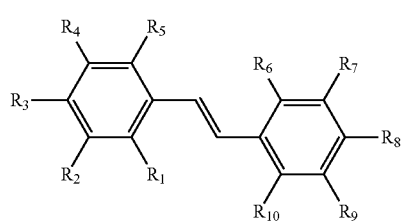

where $R_1$-$R_{10}$ are independently selected from hydrogen, alkyl, substituted alkyl, aryl, substituted aryl, —COOH, and —$NO_2$.

Alternatively, the photobleachable chromophores may comprise azobenzene chromophores of Formula (IV):

Formula (IV)

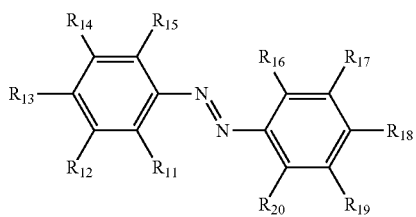

where $R_{10}$-$R_{20}$ are independently selected from hydrogen, alkyl, substituted alkyl, aryl, substituted aryl, —COOH, —$NO_2$, halogen, amino, and substituted amino.

In other embodiments, at least one chromophore must absorb more than one photon for photobleaching of the chromophore to occur.

Disclosed in still other embodiments is a method of altering the optical power of a lens, comprising: providing a lens comprising: a single polymer matrix having crosslinkable pendant groups, wherein the polymer matrix increases in volume when crosslinked; and wherein the lens is devoid of free monomers; and exposing a portion of the lens to radiation, causing crosslinking to occur in the exposed portion of the lens and changing the refractive index of the exposed portion of the lens, thereby altering the optical power of the lens.

The exposed portion of the lens may be in the center of the lens. The radiation to which the lens is exposed may have a wavelength of from about 200 nm to about 600 nm.

In other embodiments is disclosed a method of altering the optical power of a lens, comprising: providing a lens comprising a polymer matrix having photobleachable chromophores; and exposing a portion of the lens to radiation, causing photobleaching to occur in the exposed portion of the lens and changing the refractive index of the exposed portion of the lens, thereby altering the optical power of the lens.

These and other non-limiting aspects and/or objects of the disclosure are more particularly described below.

BRIEF DESCRIPTION OF THE DRAWINGS

The following is a brief description of the drawings, which are presented for the purposes of illustrating the disclosure set forth herein and not for the purposes of limiting the same.

FIGS. 9A-9C are three figures describing bleaching via two-photon absorption by a chromophore.

FIG. 10 is a cross-sectional view of an exemplary embodiment of a lens of the present disclosure.

DETAILED DESCRIPTION

Figure 1A:
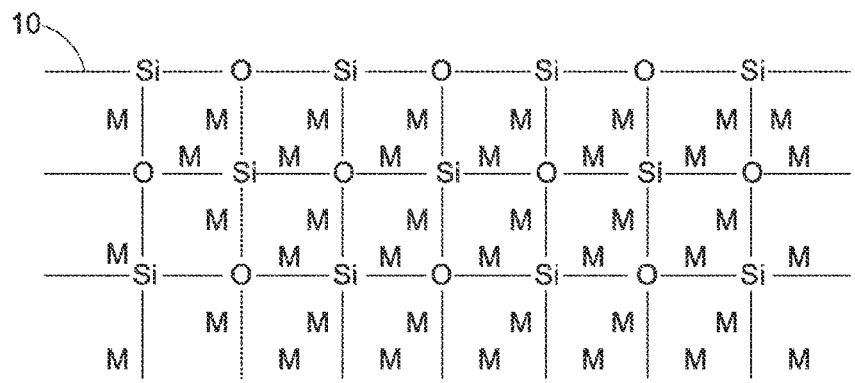
FIGS. 1A-1D are illustrations of a conventional method for adjusting lens optical power.
Figure 1B:
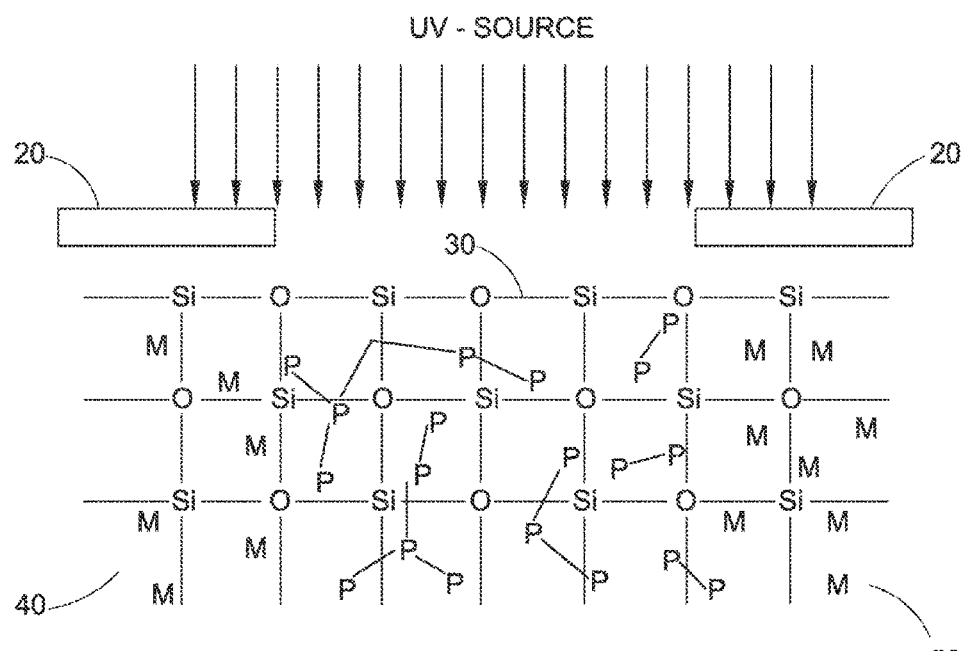
Figure 1C:
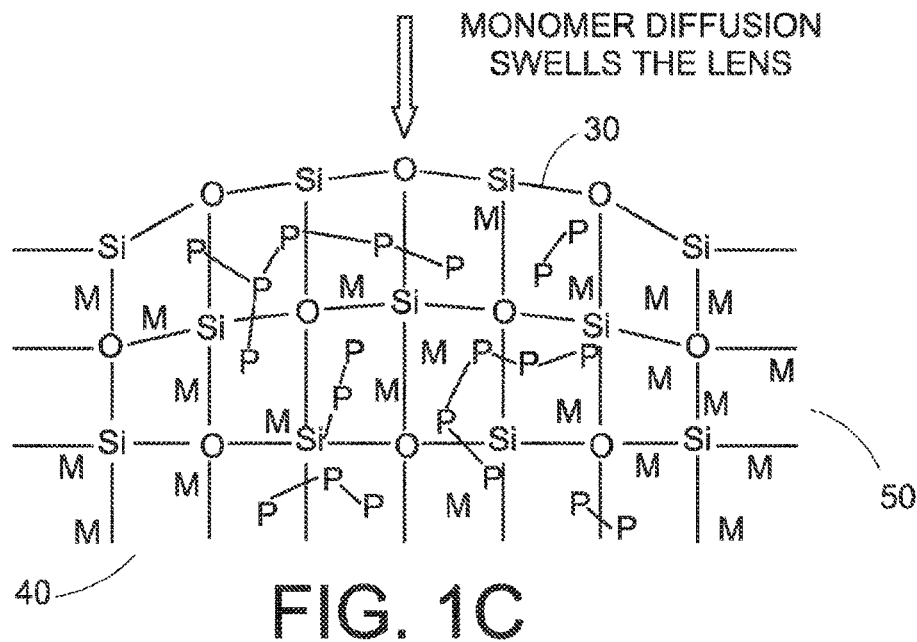
Figure 1D:
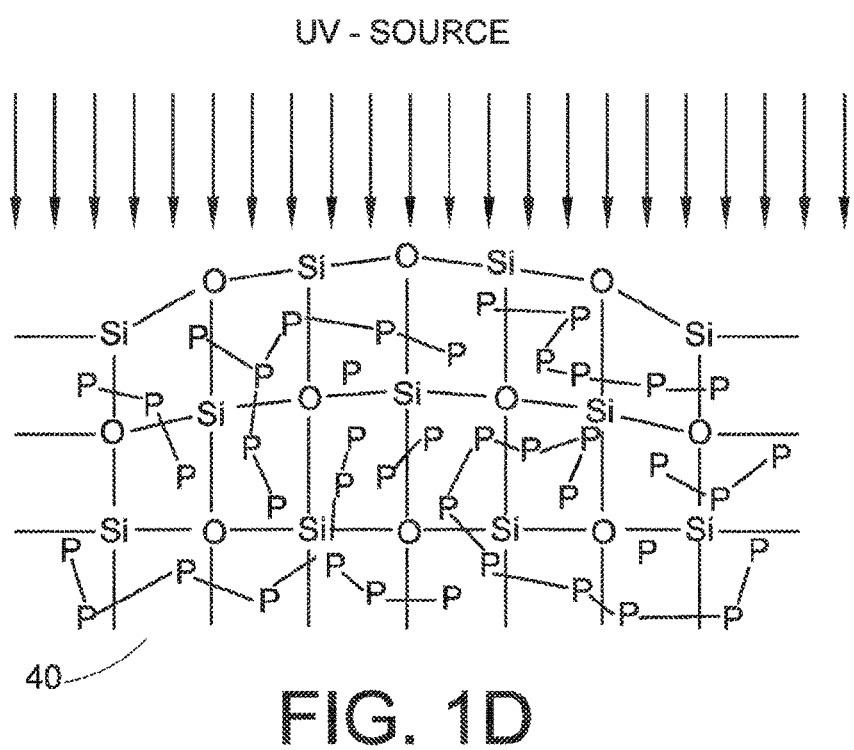

A more complete understanding of the processes and apparatuses disclosed herein can be obtained by reference to the accompanying drawings. These figures are merely schematic representations based on convenience and the ease of demonstrating the existing art and/or the present development, and are, therefore, not intended to indicate relative size and dimensions of the assemblies or components thereof.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function.

The modifier "about" used in connection with a quantity is inclusive of the stated value and has the meaning dictated by the context (for example, it includes at least the degree of error associated with the measurement of the particular quantity). When used with a specific value, it should also be considered as disclosing that value. For example, the term "about 2" also discloses the value "2" and the term "from about 2 to about 4" also discloses the range "from 2 to 4."

References to ultraviolet or UV radiation should be understood as referring to the portion of the light spectrum having wavelengths between about 400 nm and about 10 nm.

The "refractive index" of a medium is the ratio of the speed of light in a vacuum to the speed of light in the medium. For example, the refractive index of a material in which light travels at two-thirds the speed of light in a vacuum is $(1/(2/3))=1.5$.

The term "chromophore" refers to a chemical moiety or molecule that has a substantial amount of aromaticity or conjugation. This aromaticity or conjugation acts to increase the absorption strength of the molecule and to push the absorption maximum to longer wavelengths than is typical for molecules that only have sigma bonds. In many cases this chromophore will act to impart color to a material. As defined here, the chromophore does not need to absorb in the visible (i.e. does not need to be colored), but can have its absorption maximum in the UV. Alternately, the chromophore could have absorption maximum in the near-IR, with no significant absorption in the visible wavelength range. The chromophore has refractive index larger than that of the base polymer.

Non-limiting examples of chromophores which act to impart color to a material include C.I. Solvent Blue 101; C.I. Reactive Blue 246; C.I. Pigment Violet 23; C.I. Vat Orange 1; C.I. Vat Brown 1; C.I. Vat Yellow 3; C.I. Vat Blue 6; C.I. Vat Green 1; C.I. Solvent Yellow 18; C.I. Vat Orange 5; C.I. Pigment Green 7; D&C Green No. 6; D&C Red No. 17; D&C Yellow No. 10; C.I. Reactive Black 5; C.I. Reactive Blue 21; C.I. Reactive Orange 78; C.I. Reactive Yellow 15; C.I. Reactive Blue 19; C.I. Reactive Blue 4; C.I. Reactive Red 11; C.I. Reactive Yellow 86; C.I. Reactive Blue 163; and C.I. Reactive Red 180.

Additional molecules which could act as a chromophore for this disclosure, but will not impart color to a material, include derivatives of oxanilides, quinones, benzophenones, benzotriazoles, hydroxyphenyltriazines, and other polyaromatic molecules. Other examples can be found in Dexter, "UV Stabilizers", Kirk-Othmer Encyclopedia of Chemical Technology 23: 615-627 (3d. ed. 1983), U.S. Pat. No. 6,244,707, and U.S. Pat. No. 4,719,248.

Other molecules which can act as chromophores for this disclosure include unsaturated molecules found in nature, such as riboflavin, lutein, b-carotene, cryptoxanthin, zeaxanthin, or Vitamin A, as examples.

The term "photobleaching" refers to a change in the chromophore induced by photochemical means. Exemplary changes may be the cleavage of the chromophore into two or more fragments, or a change in the bond order of one or more covalent bonds in the chromophore, or a rearrangement of the bonds, such as a transition from a trans-bonding pattern to a cis-bonding pattern. Alternately, the change could be the cleavage of a bond such that the chromophore is no longer covalently bound to the polymer matrix, allowing the chromophore to be removed during wash steps.

The term "optical lens" is used herein to refer to a device through which vision can be modified or corrected, or through which the eye can be cosmetically enhanced (e.g. by changing the color of the iris) without impeding vision. Non-limiting examples of optical lenses include eyewear and ophthalmic lenses. The term "ophthalmic lenses" refers to those devices that contact the eye. Examples of ophthalmic lenses include contact lenses and intraocular lenses. Examples of eyewear include glasses, goggles, full face respirators, welding masks, splash shields, and helmet visors.

The optical power of a simple lens is given by the following Equation 1:

$$\frac{1}{f} = (n - n_0)\left[\frac{1}{R_1} - \frac{1}{R_2} + \frac{(n - n_0)d}{nR_1R_2}\right] \quad (1)$$

where $1/f$ is the optical power of the lens (measured in diopters or $m^{-1}$), $n$ is the refractive index of the lens material, $n_0$ is the refractive index of the surrounding medium, $R_1$ and $R_2$ are the two radii of curvature of the lens, and $d$ is the thickness of the lens.

Figure 2:
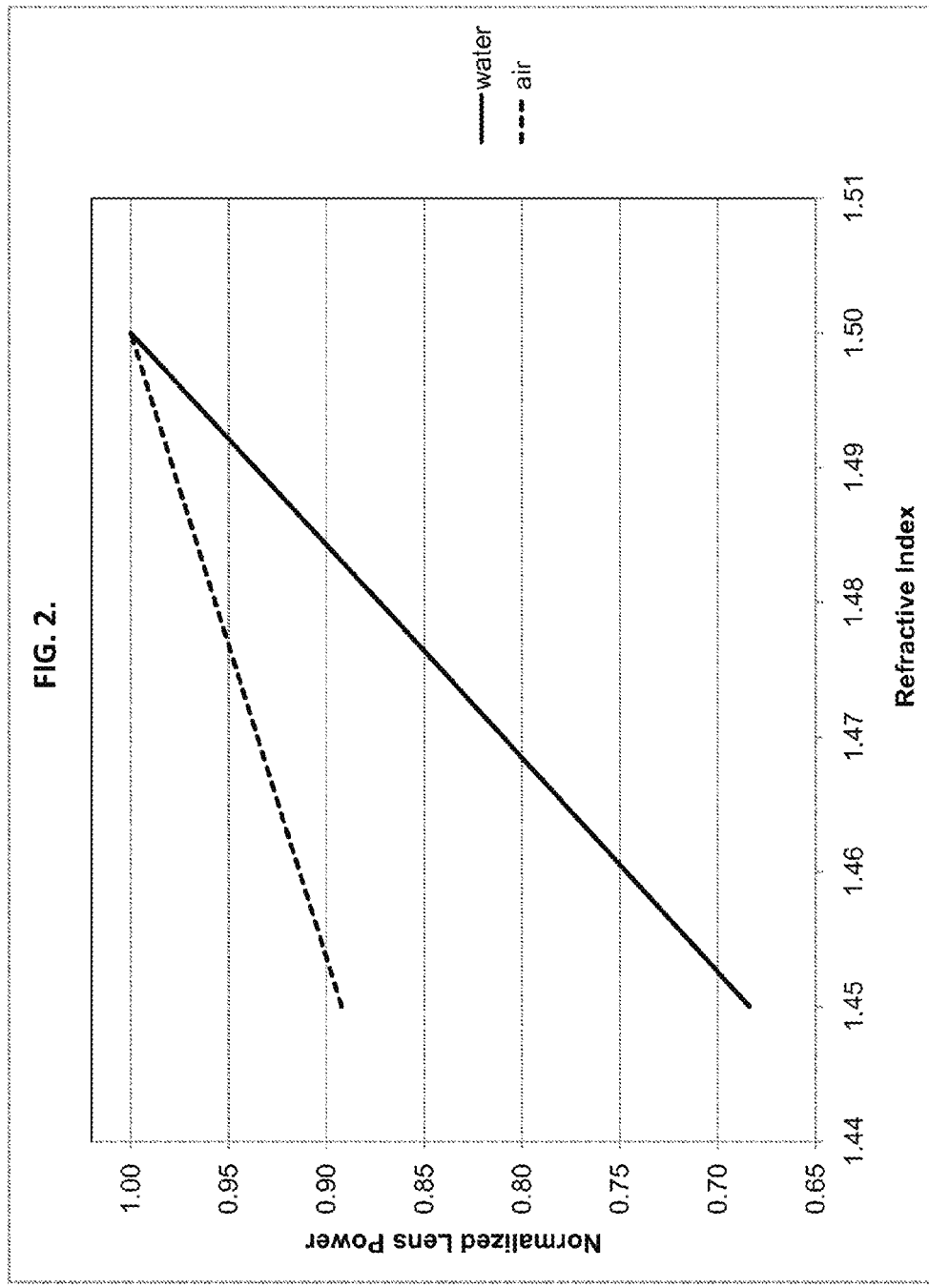
FIG. 2 is a graph showing a normalized change in lens optical power as a function of the refractive index of the lens in both air and water.

The importance of change in the refractive index is shown in FIG. 2, which is a graph showing the normalized change in lens optical power as a function of the refractive index for a lens placed both in water and air (normalized by the lens power at n=1.5). The calculations were performed using $R_1$=0.00185 m, $R_2$=0.00255 m, d=300 μm, $n_0$ for water=1.3374, and $n_0$ for air=1.0000.

Figure 3A:
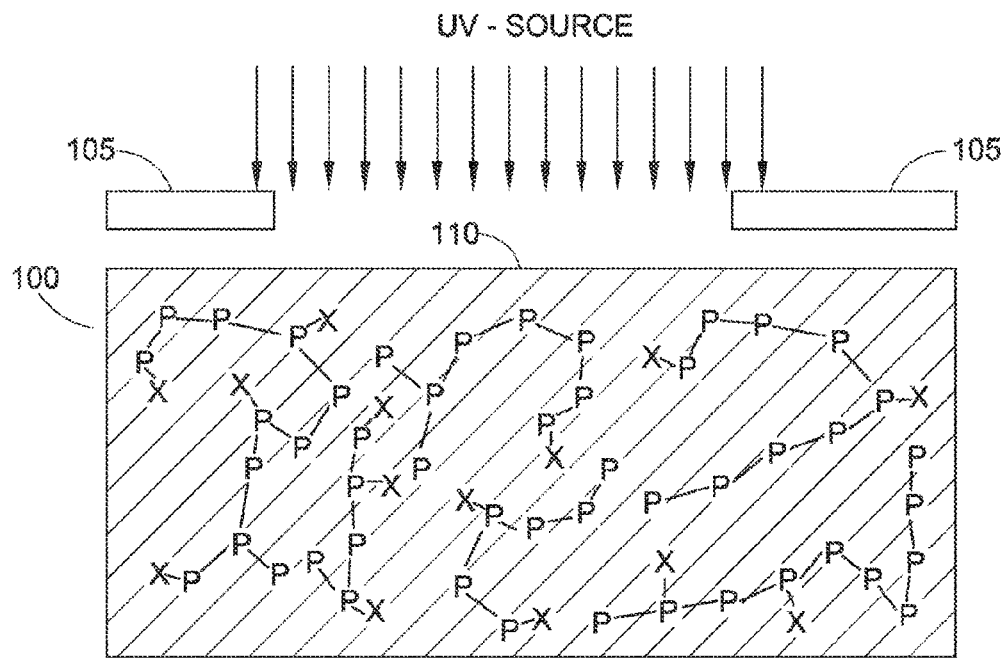
FIGS. 3A-3B are illustrations of one method of the present disclosure for altering the optical power of a lens.
Figure 3B:
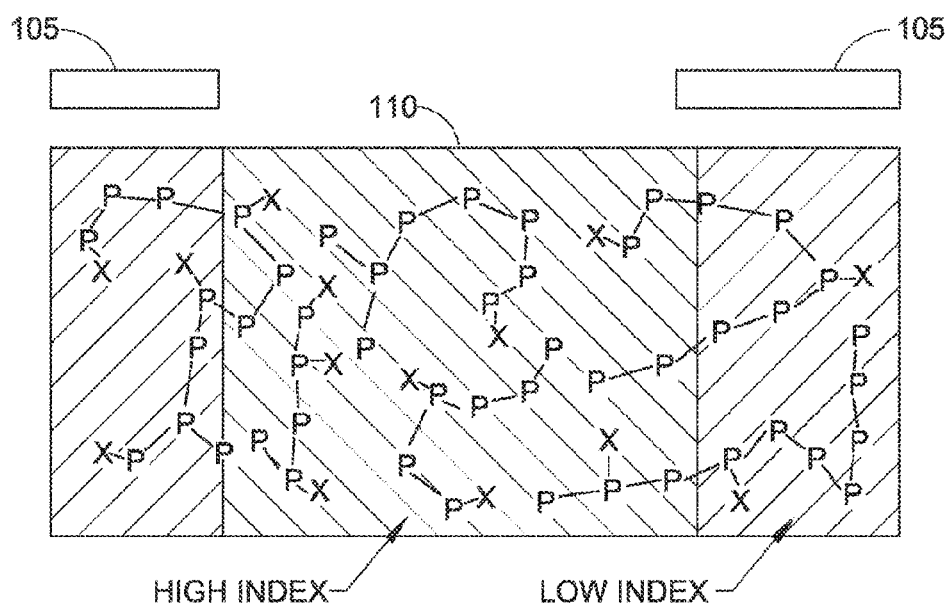

In some methods of the present disclosure, crosslinking is used to change the refractive index of the lens. The lens thickness may either slightly shrink or increase, but the lens curvature is not appreciably altered. The primary change in lens optical power comes from the change in refractive index, not from the change in lens thickness or curvature. This is illustrated in FIG. 3. In FIG. 3A, the lens 100 contains a polymer matrix (denoted as P) having crosslinkable pendant groups (denoted as X). A mask 105 is used to expose only a portion 110 of the lens to UV or other radiation. As seen in FIG. 3B, crosslinking occurs in the exposed portion 110 of the lens, changing the refractive index of the exposed portion.

A lens which is useful in this method may comprise a conventional polymer capable of behaving as a hydrogel, i.e. which can swell upon contact with water. Typically, crosslinking a conventional polymer decreases the volume of the polymer, similar to the decrease in volume upon polymerization (i.e. a decrease in thickness occurs). This reduction in volume leads to an increased refractive index. However, there are monomers, such as 3,9-divinyl-2,4,8,10-tetraoxy-spiro[5.5]undecane (shown below), which expand under photopolymerization.

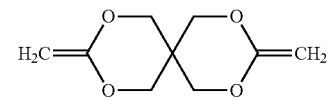

3,9-divinyl-2,4,8,10-tetraoxy-spiro[5.5]undecane

Including similar functional groups as reactive sidechains or pendant groups in the polymer may lead to an increase in volume upon crosslinking. After crosslinking these functional groups, the regions where the polymer volume has increased will have decreased refractive index, while areas where the polymer volume decreases will have increased refractive index. Put another way, the crosslinked regions of the lens have increased refractive index.

Alternatively, crosslinking a hydrogel controls the degree to which it can swell in the presence of water, preventing an increase in volume. After crosslinking, those regions where the hydrogel has been crosslinked will have an increased refractive index compared to the regions where the hydrogel has not been crosslinked.

Because the change in lens optical power of such lenses does not rely on diffusion of free monomers, the change in lens power can be monitored in real time. Millan in Polymer 46 (2005), pp. 5556-5568, discloses a crosslinked polystyrene which increases refractive index and thickness after crosslinking.

One approach to approximate the role of crosslinking on the optical properties of polymers is to use the Lorentz-Lorenz formalism, which expresses the refractive index in terms of a molar refractivity $R_{LL}$ and molar volume V, as in Equation 2:

$$n = \left[\frac{1+2R_{LL}/V}{1-2R_{LL}/V}\right]^{1/2} \quad (2)$$

Figure 4:
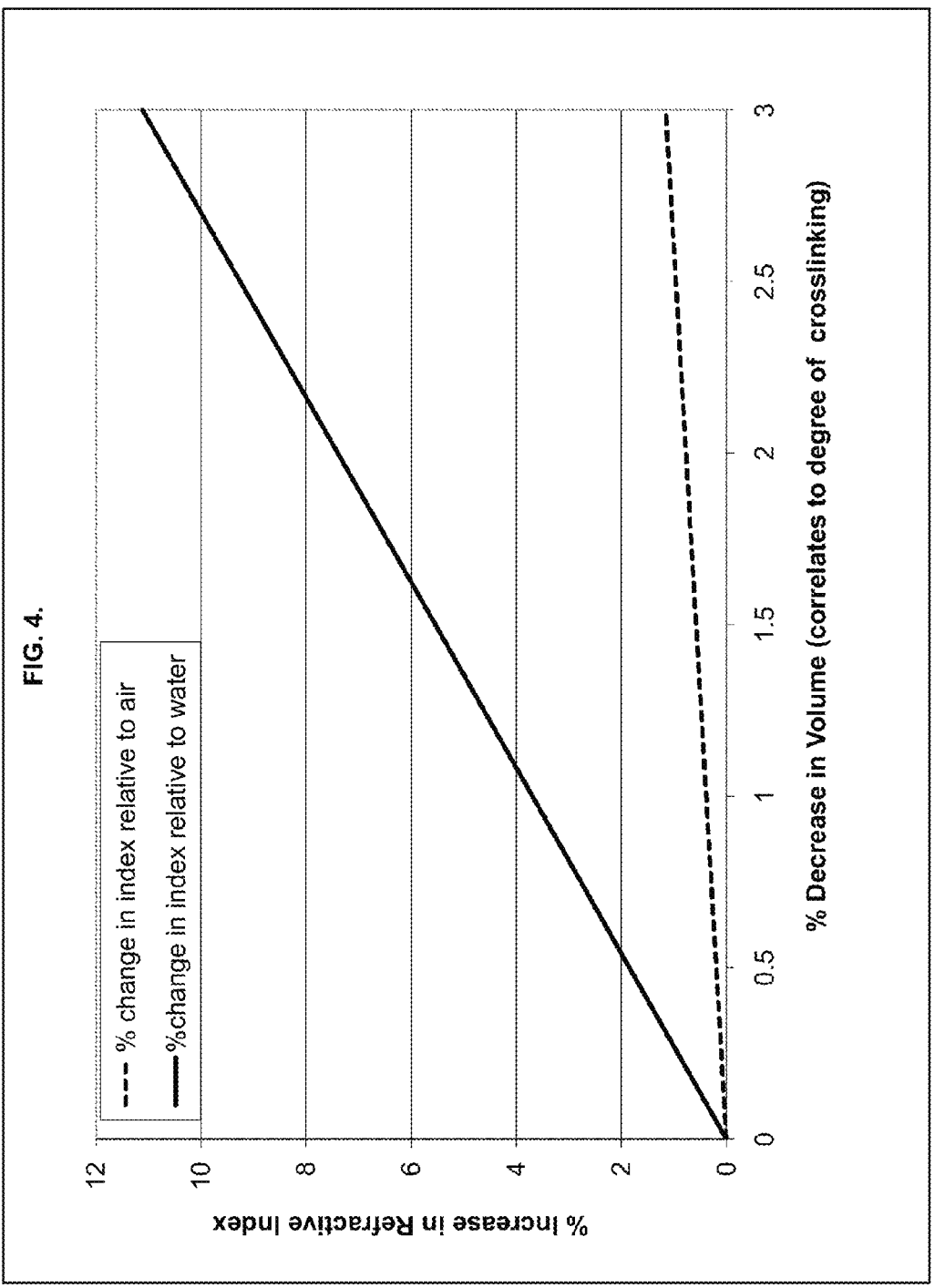
FIG. 4 is a graph showing the change in the refractive index as a function of the change in the volume of a polymer used to make the lens.
Figure 5:
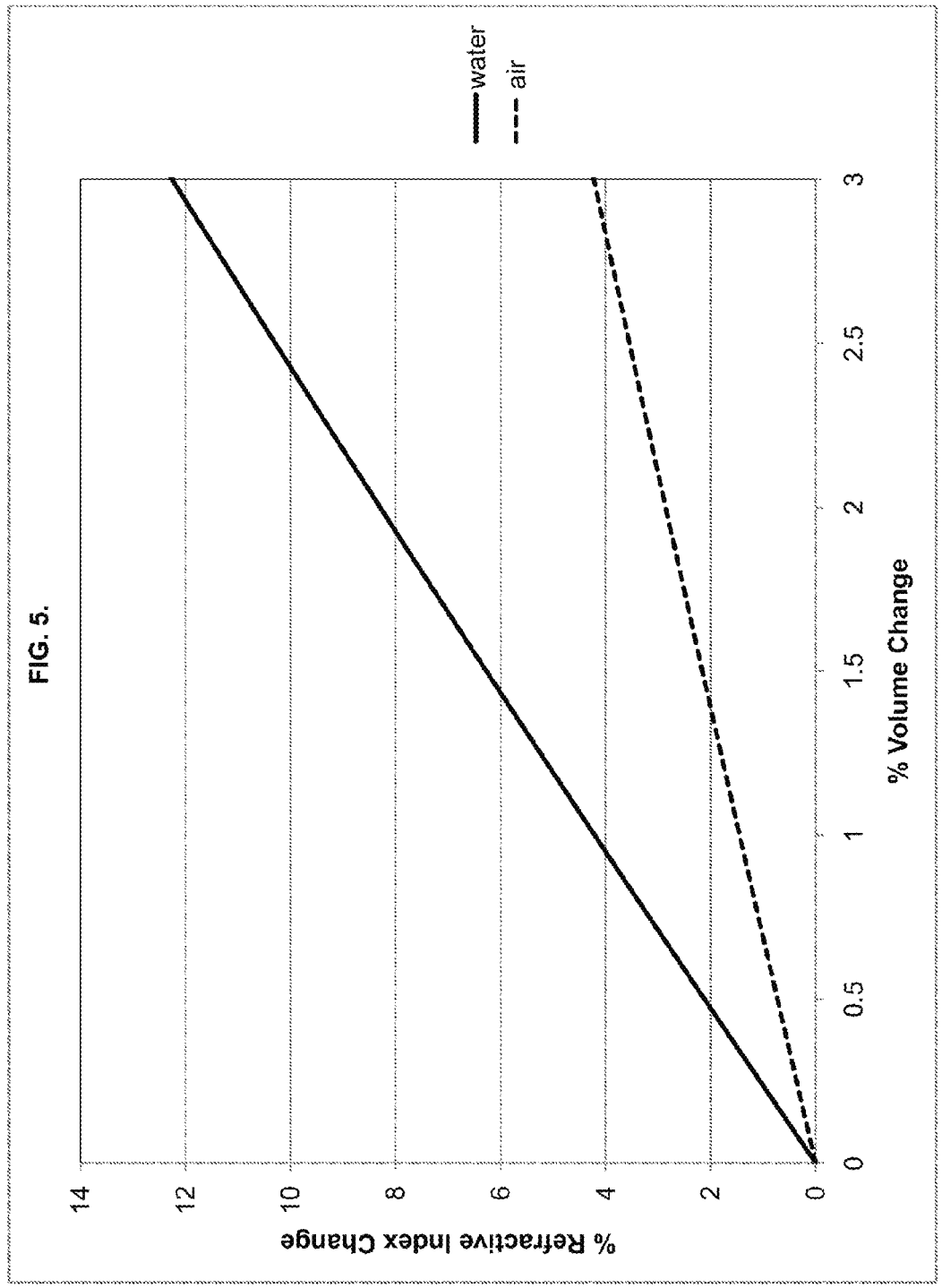
FIG. 5 is a graph showing the change in the lens optical power as a function of the change in the volume of a polymer used to make the lens.

The effect of crosslinking is then treated as solely altering the molar volume, without changing the molar refractivity. FIG. 4 shows the change in the refractive index associated with a change in the volume using Equation 2. FIG. 5 shows the change in the lens power as a function of the change in volume. The calculations were performed using polymethyl methacrylate (PMMA) as the model compound, with MW=100.117, $R_{LL}$=24.754, and starting volume of V=865 (see van Krevelen, Properties of Polymers, 1976). The volume was systematically decreased and the refractive index was calculated. The lens power calculations were again performed using $R_1$=0.00185 m, $R_2$=0.00255 m, d=300 μm, $n_0$ for water=1.3374, and $n_0$ for air=1.0000. The calculated refractive index started at n=1.48415, and ended at n=1.50129 (Ln=0.01714, 1.15%).

FIG. 5 shows that a change of up to about 10% in lens optical power can occur for a change in volume of less than about 3%, corresponding to a thickness change in the lens of less than about 1%. The calculations are fairly insensitive to whether the volume change is modeled as just corresponding to a thickness change, or is modeled as changing in all 3 dimensions equally.

In embodiments, the lens suitable for practicing this method may comprise a single polymer matrix containing crosslinkable pendant groups, wherein the polymer matrix increases in volume when crosslinked. The lens does not contain free monomers that diffuse between regions to increase the volume. Rather, the increase in volume is due to diffusion of water into the exposed (i.e. crosslinked) portion of the lens.

In embodiments, a method for altering the optical power of a lens comprises providing a lens comprising a single polymer matrix having crosslinkable pendant groups, wherein the polymer matrix increases in volume when crosslinked. The lens is devoid of, i.e. does not contain, free monomers. A portion of the lens is exposed to radiation, such as ultraviolet radiation. This causes crosslinking to occur in the exposed portion of the lens and changes the refractive index of the exposed portion. The refractive index may increase or decrease, and decreases in particular embodiments. In particular embodiments, the exposed portion is in the center of the lens.

Figure 6A:
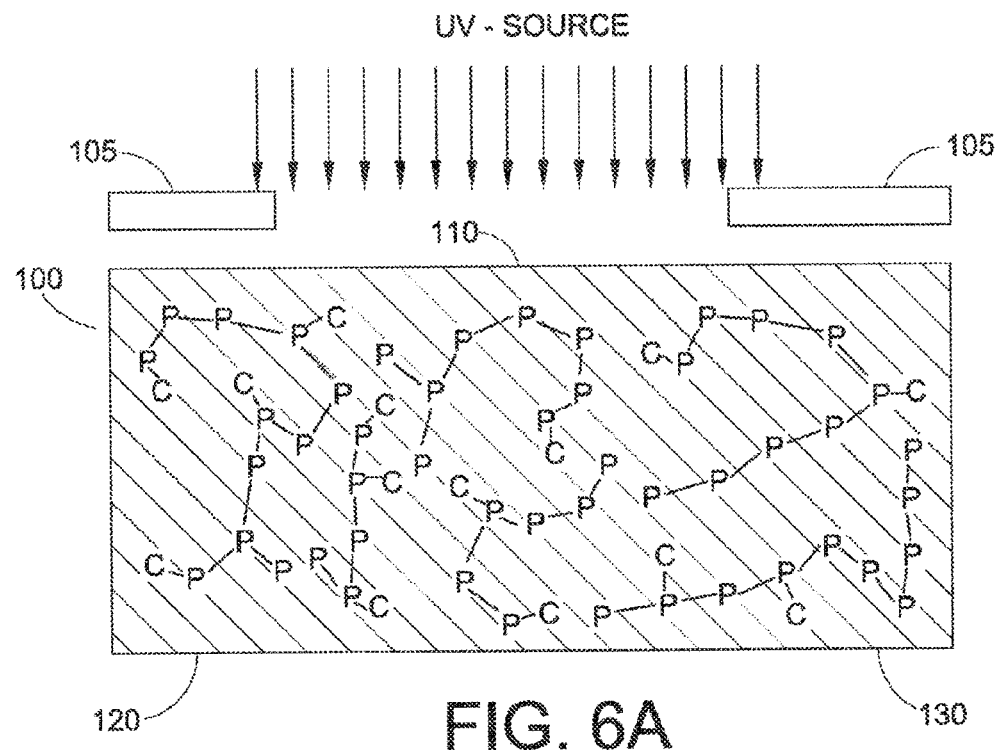
FIGS. 6A-6B are illustrations of another method of the present disclosure for altering the optical power of a lens.
Figure 6B:
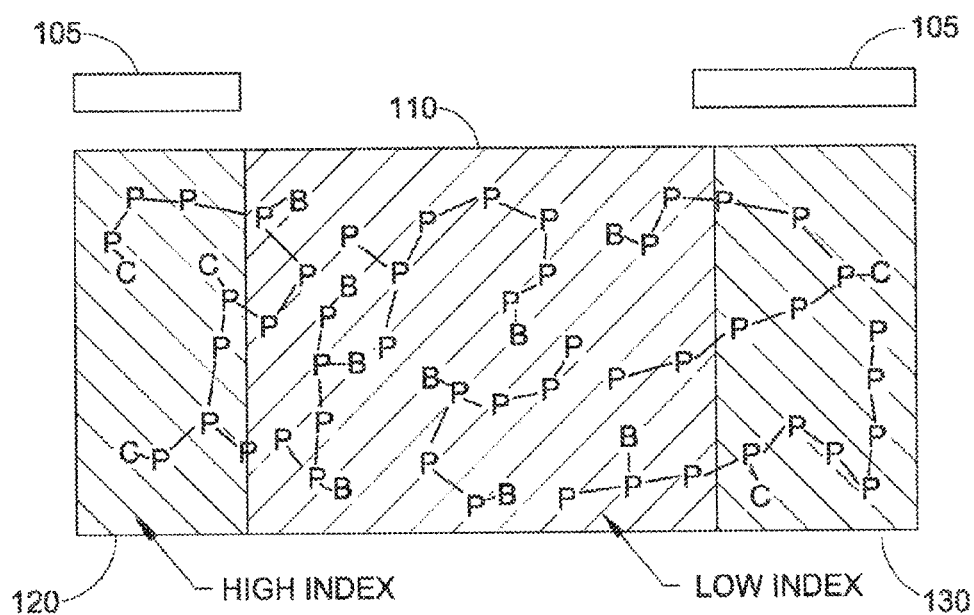

In other methods of the present disclosure, ultraviolet (UV) radiation is used to photobleach the lens material. Certain aromatic groups, such as naphthalene, can degrade under UV radiation exposure. This leads to a decrease in the refractive index in these exposed regions, without any change in lens thickness. FIG. 6 is a schematic of the photobleaching process. In FIG. 6A, the lens 100 contains a polymer matrix (denoted as P) having photobleachable chromophores (denoted as C). A mask 105 is used to expose only a portion 110 of the lens to UV or other radiation. As seen in FIG. 6B, the chromophores in the exposed portion 110 of the lens are bleached (denoted as B), lowering the refractive index of the exposed portion compared to the unexposed portions 120, 130. Photobleaching has exceptional spatial resolution, commonly on the order of a few microns. There is extensive literature on the design of chromophores to photobleach and on the design of optical materials with enhanced photostability.

The photobleaching of a material can be described using Equation 3:

$$\frac{B}{\sigma} = \tau n \quad (3)$$

where B is the probability of the degradation event happening, σ is the cross section, n is the photon flux, and τ is the lifetime of the chromophore. B/σ is often referred to as the photostability Figure-of-Merit (FOM). B/σ has strong energy dependence and also strong dependence on the maximum absorption wavelength ($\lambda_{max}$) of the chromophore.

The energy dependence can be approximated with Equation 4:

$$\log\left[\frac{B}{\sigma}\right] = 24 + 5.0 \times (E_{max} - E) \quad (4)$$

where $E_{max}$, is the energy of the chromophore maximum absorption wavelength.

Figure 7:
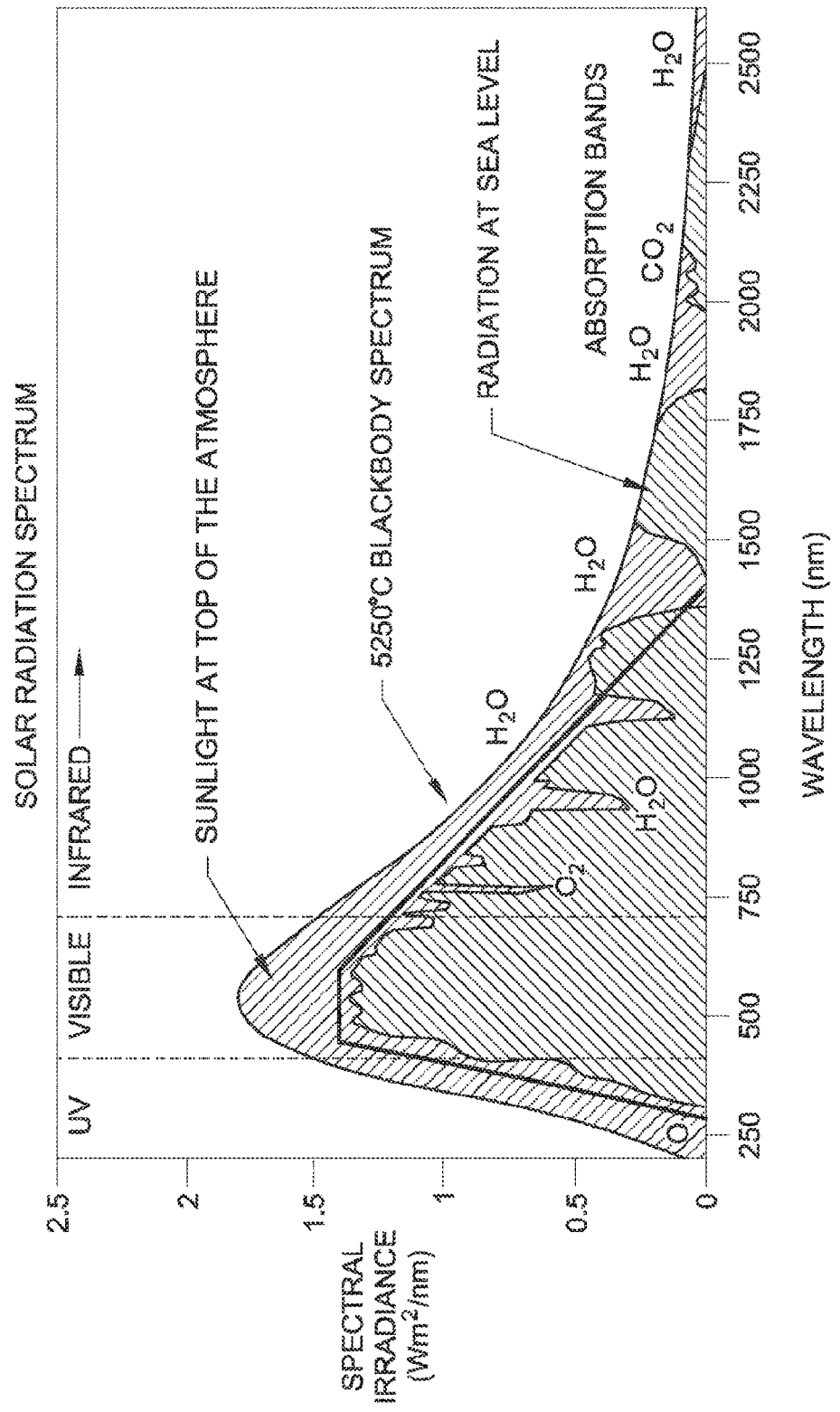
FIG. 7 is a graph of the solar spectrum, showing the amount of energy at each wavelength.

The next step in the chromophore lifetime calculation is determination of the maximum and average photon flux the lens will be exposed to. The solar spectrum has the form of FIG. 7, and is approximated by the solid line. Long wavelength radiation will be ignored in the determination, as it will have no effect on the photodegradation.

Figure 8:
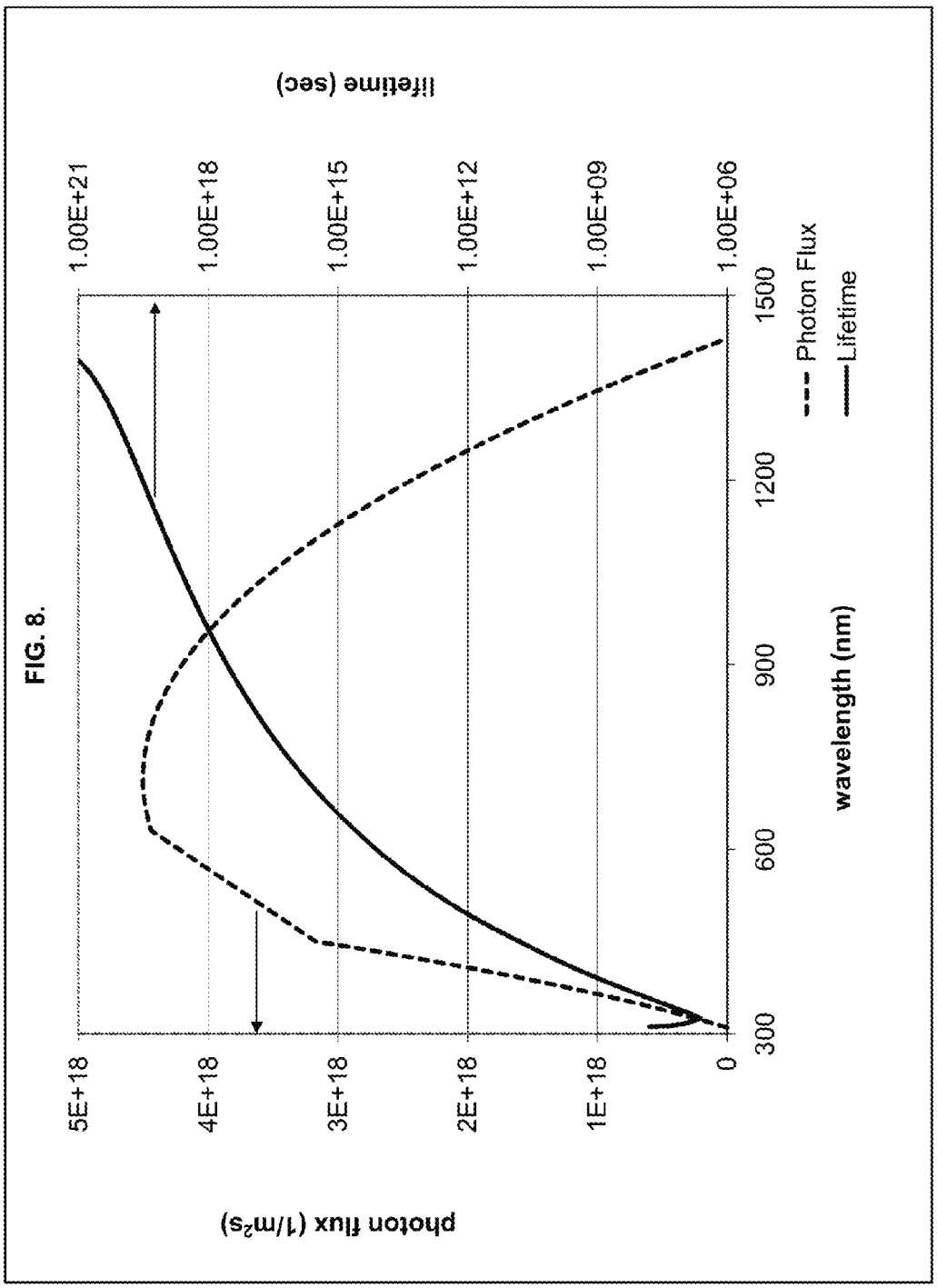
FIG. 8 is a graph showing the photon flux and the chromophore lifetime as a function of the wavelength.

After conversion of the solar spectrum into photon flux, and using the energy dependent FOM expression assuming chromophore absorption maximum of 325 nm, the plot of the chromophore lifetime as a function of the energy in the solar spectrum can be obtained, and is shown as FIG. 8. The solid line is the chromophore lifetime, while the dotted line is the photon flux.

The total chromophore lifetime is obtained from the summation of the inverse lifetimes (the total degradation rate is the sum of the individual degradation rates). In this example, the total chromophore lifetime is calculated to be about $2.1 \times 10^5$ seconds. Notably, there is a rapid increase in lifetime as the wavelength increases. Much less than 1% of the photodegradation in this example arises from wavelengths longer than about 400 nm.

The previous calculation for the total chromophore lifetime assumes that the user stares directly into the noontime sun for the entire lens lifetime, which overestimates the total photon exposure during the lens lifetime. Using an ambient light level of 32,000 lux (average noontime level) for 9 hours, 9 hours of 400 lux (ambient office lighting) and 6 hours of sleep per day, the photon flux is calculated to be overestimated by a factor of 30, leading to a predicted lifetime for the lens of about $6.2 \times 10^6$ seconds. This lifetime is still shorter than desired ($2 \times 10^9$ seconds is desired), but literature precedent shows straight-forward methods to increase the lifetime by more than the three orders of magnitude needed.

The final issue is the amount of optical power available for the photobleaching. Based on 2006 Trans. Am. Ophthalmol. Soc. p. 29, where a power of 12 mW/cm$^2$ was used for 120 seconds (A=365 nm), the photon flux is $2.2 \times 10^{20}$/(m$^2$·sec), and the total photon exposure is $2.7 \times 10^{22}$/m$^2$. Staring into the sun, the photon flux below 400 nm is $7.6 \times 10^{19}$/(m$^2$·sec), the ambient noontime flux below 400 nm is approximately $2.5 \times 10^{19}$/(m$^2$·sec), and the average flux is $2.5 \times 10^{18}$/(m$^2$·sec).

In embodiments, a lens suitable for practicing this method comprises a polymer matrix containing photobleachable chromophores. The chromophores may be present as compounds dispersed within the polymer matrix or as pendant groups on the polymer matrix. The chromophores may contain a reactive site which can react with a reactive site on the polymer matrix to allow crosslinking.

In particular embodiments, the chromophore contains a malononitrile moiety. Exemplary chromophores include those of Formulas (I) and (II), which are also known as VC60 and EC24, respectively:

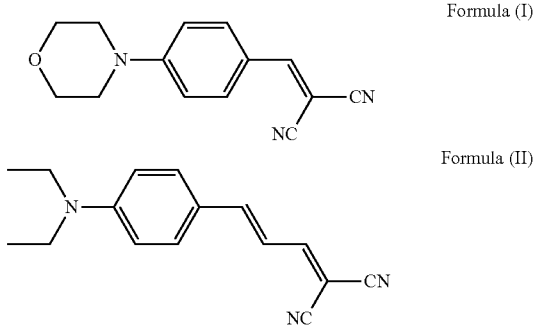

Formula (I)

Formula (II)

Formula (I) may also be called 4-morpholinobenzylidene malononitrile. Formula (II) may also be called 2-[3-(4-N, N-diethylanilino)propenylidene] malononitrile.

In other embodiments, the chromophore is a stilbene compound of Formula (III):

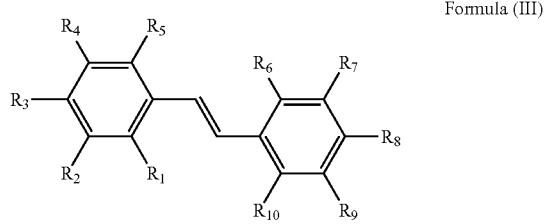

Formula (III)

where $R_1$-$R_{10}$ are independently selected from hydrogen, alkyl, substituted alkyl, aryl, substituted aryl, —COOH, and —NO$_2$.

The term "alkyl" as used herein refers to a radical which is composed entirely of carbon atoms and hydrogen atoms which is fully saturated. The alkyl radical may be linear, branched, or cyclic. Linear alkyl radicals generally have the formula —C$_n$H$_{2n+1}$.

The term "aryl" refers to an aromatic radical composed of carbon atoms and hydrogen atoms. When aryl is described in connection with a numerical range of carbon atoms, it should not be construed as including substituted aromatic radicals. For example, the phrase "aryl containing from 6 to 10 carbon atoms" should be construed as referring to a phenyl group (6 carbon atoms) or a naphthyl group (10 carbon atoms) only, and should not be construed as including a methylphenyl group (7 carbon atoms). The term "heteroaryl" refers to an aryl radical which is not composed of entirely carbon atoms and hydrogen atoms, but rather also includes one or more heteroatoms. The carbon atoms and the heteroatoms are present in a cyclic ring or backbone of the radical. The heteroatoms are selected from O, S, and N. Exemplary heteroaryl radicals include thienyl and pyridyl.

The term "substituted" refers to at least one hydrogen atom on the named radical being substituted with another functional group selected from halogen, —CN, —NO$_2$, —COOH, and —SO$_3$H. An exemplary substituted alkyl group is a perhaloalkyl group, wherein one or more hydrogen atoms in an alkyl group are replaced with halogen atoms, such as fluorine, chlorine, iodine, and bromine. Besides the aforementioned functional groups, an alkyl group may also be substituted with an aryl group. An aryl group may also be substituted with alkyl. Exemplary substituted aryl groups include methylphenyl and trifluoromethylphenyl.

Generally, the substituents $R_1$-$R_{10}$ are selected to enhance other properties of the chromophore. For example, $R_1$, $R_5$, $R_6$, or $R_{10}$ could be selected to be a crosslinkable group, such as a carboxylic acid. The substituents may also be selected as to control the absorption maximum and/or the refractive index of the chromophore, such as trifluoromethyl (to lower the refractive index), or a nitro group (to redshift the absorption maximum). The substituents may also be selected to enhance the photostability of the chromophore. For example, inclusion of a bulky group at the 2 or 2' position, such as phenyl, inhibits trans-cis isomerization.

In other embodiments, the chromophore is an azobenzene compound of Formula (IV):

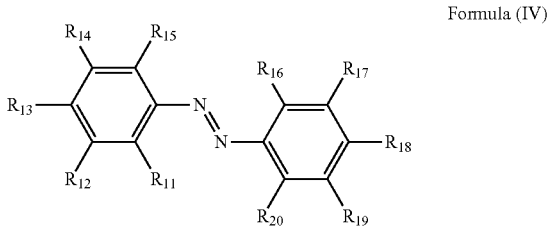

Formula (IV)

where $R_{10}$-$R_{20}$ are independently selected from hydrogen, alkyl, substituted alkyl, aryl, substituted aryl, —COOH, —NO$_2$, halogen, amino, and substituted amino. Generally, the substituents $R_{10}$-$R_{20}$ are selected to enhance other properties of the chromophore.

The term "amino" refers to —NH$_2$.

In still other embodiments, the chromophore must absorb more than one photon for bleaching to occur. FIG. 9 provides an explanation. As illustrated in FIG. 9A, the chromophore molecule has three energy levels, which include the ground state G, the first excited state B which can be accessed from the ground state by the absorption of a single photon $\omega_{max}$, and the second excited state A which cannot be accessed from the ground state by a single photon absorption. Typically, there is an allowed transition between states B and A. The second excited state A is the state where the chromophore bleaches. Analysis of the one and two photon absorption spectra for simple chromophores indicates that the energy of state B relative to the ground state is approximately 0.85 of the energy of state A relative to the ground state (Marius Albota, *Science* 281, p. 1653 (1998)). FIG. 9B shows the energy spectrum for a standard two-photon absorption. In this process, two photons w of the same wavelength are absorbed, when the energy of a single photon is too small to be directly absorbed. In this case, the absorption rate depends on the square of the optical intensity. It is also possible to have a two photon absorption where the two photons are of different frequencies. This is shown in FIG. 9C, where two distinct photons ω1 and ω2 are absorbed, even though neither photon alone has sufficient energy to excite the molecule to even the first excited state B. In this case, the absorption intensity is proportional to the product of the intensity of each wavelength.

In embodiments, a method for altering the optical power of a lens comprises providing a lens comprising a polymer matrix containing photobleachable chromophores. A portion of the lens is exposed to radiation, such as ultraviolet radiation. This causes photobleaching to occur in the exposed portion of the lens and changes the refractive index of the exposed portion. The refractive index may increase or decrease, and decreases in specific embodiments. In particular embodiments, the exposed portion is in the center of the lens.

After the optical power of the lens is altered, the lens must be stabilized to prevent further undesired changes. Previous lenses which include free monomer(s) typically used partial polymerization, allowed the free monomer(s) to diffuse, then did a complete polymerization to preclude any further change in the shape of the lens or the refractive index. The present disclosure contemplates at least three methods of stabilization.

Figure 11:
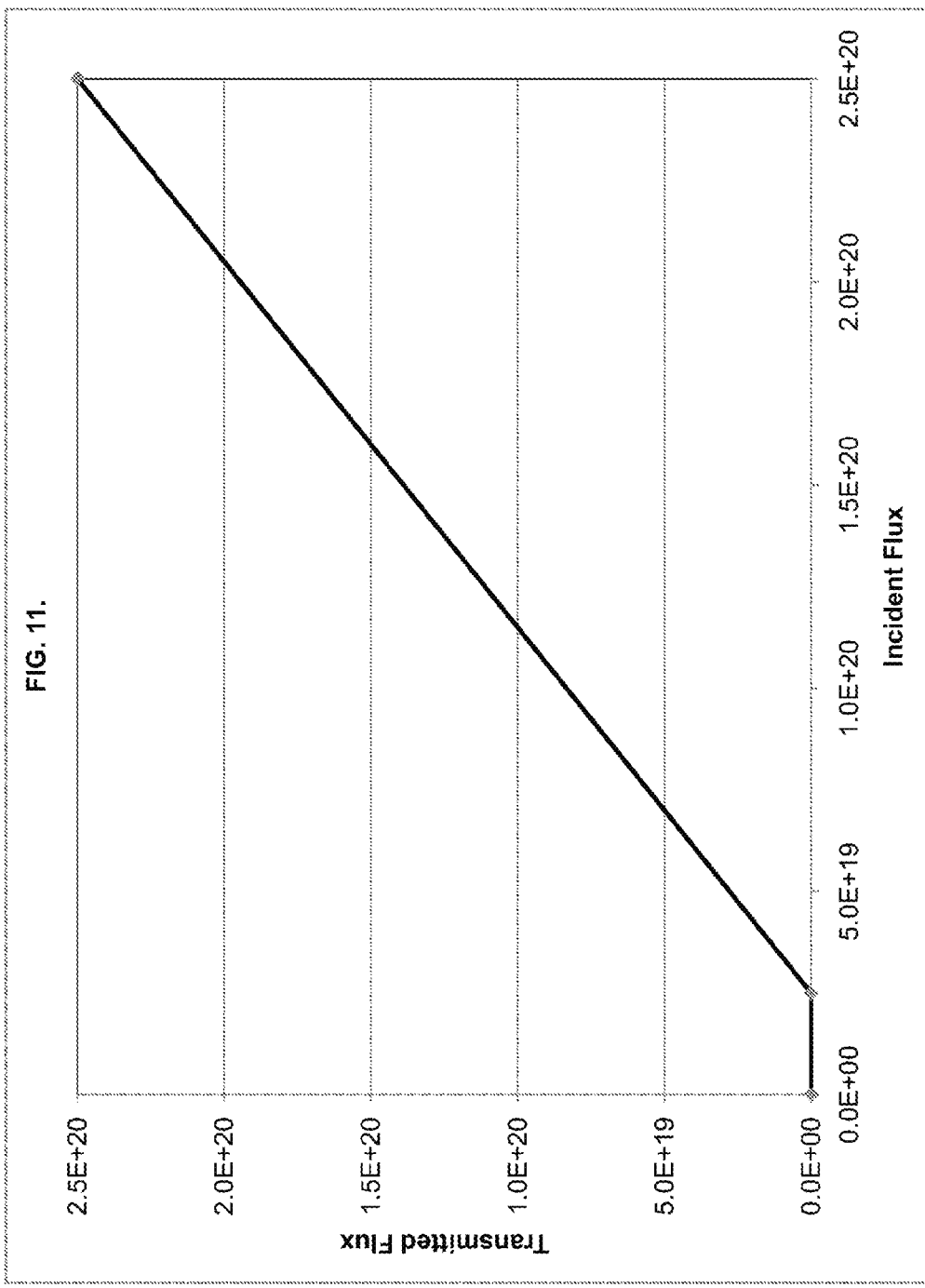
FIG. 11 is an idealized transmission spectrum for a UV radiation absorbing layer of the present disclosure.

First, a UV radiation absorbing layer may be laid over at least one surface of the lens. The UV radiation absorbing layer ideally almost completely absorbs short wavelength photons at low UV intensity, but passes most photons at high UV intensity. An exemplary lens is shown in FIG. 10. Here, the lens 200 comprises a polymer matrix 210 and UV radiation absorbing layers 220, 230 on each surface 212, 214 of the polymer matrix. An idealized transmission spectrum at the bleaching wavelength and longer is shown in FIG. 11. At wavelengths shorter than the bleaching wavelength, the UV absorption layer completely absorbs photons. At the bleaching wavelength and longer, however, the photon absorption depends on the incident flux. At low levels of incident UV intensity, i.e. that of natural illumination, the transmitted flux (i.e. the number of photons passing through the UV absorption layer) is low or zero. At higher levels of incident UV intensity, however, i.e. applied illumination, the transmitted flux increases. This difference allows the lens to be adjusted after implantation by the application of artificial radiation, then prevent further adjustment during natural use. This UV absorbing layer can be used with both types of lenses described above.

The second stabilization method involves crosslinking the chromophore to the polymer matrix, through for example the 2' position. The chromophore can be attached to the polymer matrix as a pendant group or sidechain with a reactive site or group on the chromophore, and a corresponding reaction site or group elsewhere on the polymer matrix. After fabrication, the lens can be stored at a temperature below the Tg of the polymer, greatly slowing the crosslinking reaction. After implantation, the chromophore will slowly crosslink with the polymer matrix, greatly enhancing its photostability. The rate of this crosslinking reaction can be controlled by altering the functionality of the reactive groups, allowing sufficient time for the lens to be adjusted. If the crosslinking occurs through a condensation reaction, water will be the only by-product. After crosslinking, there will be a further reduction in the rate at which the isomerization can occur, further enhancing photostability.

Crosslinking the chromophore through its 2' position is significant because of the degradation mechanism of, for example, stilbene chromophores. The primary degradation pathway of stilbene chromophores is through oxidation of the central double bond after a trans-cis isomerization. Thus, blocking groups have also shown an increase in the chromophore stability. As shown in the following diagram, the unsubstituted stilbene can undergo trans-cis isomerization, while the substituted stilbene is sterically hindered. By hindering isomerization, stability is increased.

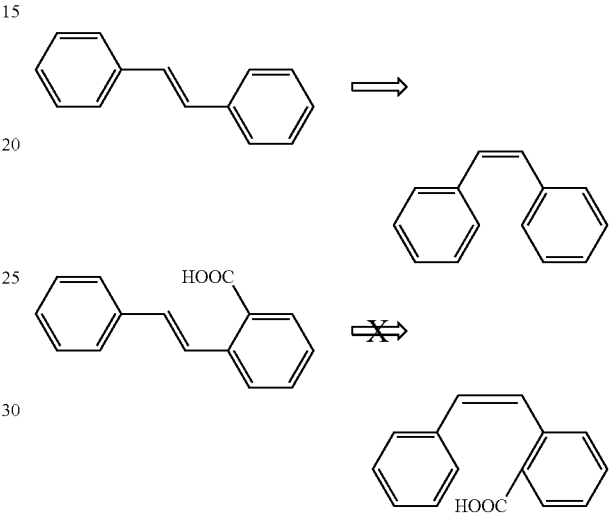

Finally, the third stabilization method uses a chromophore which bleaches under specific conditions. In particular, a chromophore which requires the absorption of more than one photon to bleach is used. The bleaching process is slow under low-level illumination, but may still occur, particularly during daytime outside exposure. However, judicious selection of the excitation wavelengths of the chromophore can slow this process even further. Referring back to FIG. 7, certain wavelengths are filtered from the solar spectrum, due to the presence of specific compounds in the atmosphere. Design of the chromophore so that one of the two wavelengths needed to cause bleaching corresponds to one of the filtered wavelengths will lead to a lens with enhanced stability, as there will be no high-intensity natural radiation at that wavelength to initiate the photodegradation.

For example, if we assume a chromophore with an absorption maximum of 400 nm, the two-photon absorption would then occur at about 340 nm. If one of the wavelengths is 1300 nm (which is strongly absorbed in the atmosphere), we can the calculate that the other wavelength needed would be 460 nm. Thus a combination of a 1300 nm photon and a 460 nm photon could be absorbed, even though neither photon will be absorbed individually. Because the 1300 nm photon is not strongly present in natural outdoor illumination, absorption and continued photobleaching would not occur.

The photostability of chromophores may also be enhanced in other ways. The chromophores may be attached to the polymer matrix as a polymer side chain or pendant group. Chromophores could be crosslinked to other functional groups on the polymer backbone or sidechains, reducing the conformational movement often needed as part of the photobleaching process. The absorption maximum wavelength could be blue-shifted. The functional groups of the chromophore could be changed to inhibit rotational motion around specific bonds, or block specific photodegradation pathways. For example, inclusion of a trifluoromethyl group at the 2 or 2' position of an azobenzene chromophore can reduce the rate at which photobleaching occurs. Finally, the local environment of the chromophore could be changed, e.g. by changing the local pH.

Several other methods of altering the optical power of a lens are also disclosed. These methods relate to lenses that use photobleachable chromophores and a polymer matrix. Generally, exposure to radiation is used to cause bleaching with different variations.

In some methods, the lens includes a polymer matrix having photobleachable chromophores and a photosensitive donor lacking photoinitiating groups. This system uses a two-photon process. In other words, the donor needs to absorb two photons to have sufficient energy to degrade the chromophores, which causes photobleaching and changes the refractive index.

The donor molecule is responsive to a first photon and generates primary excited state donor molecules which are not responsive to the first wavelength of energy. However, the primary excited state donor molecules are responsive to a sequentially applied second photon that generates secondary higher energy level excited state donor molecules.

The chromophores have a lowest primary excited state energy greater than the primary excited state energy of the photosensitive donor molecules. Thus, the chromophores cannot receive energy from the primary excited state donor molecules that would cause degradation. Only when secondary higher energy level excited state donor molecules are generated can the chromophores accept energy to reach an excited state that causes degradation of the chromophore. This results in photobleaching and the refractive index to be changed, thus altering the optical power of the lens.

The two photons absorbed by the donor may be of the same wavelength (degenerate) or of different wavelengths (non-degenerate). In regard to the non-degenerate method, it is contemplated that a first portion of the lens is exposed to radiation at the first wavelength, and a second portion of the lens is exposed to radiation at the second wavelength. The second portion completely overlaps the first portion, or in other words the first portion can be of a larger area than the second portion.

The photosensitive donor may be selected from chromophores with large degenerate two-photon absorption such as those illustrated in Formulas (A)-(E):

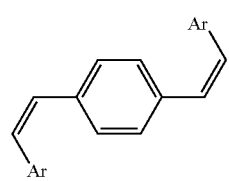

FIG. (A)

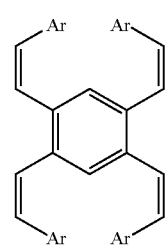

FIG. (B)

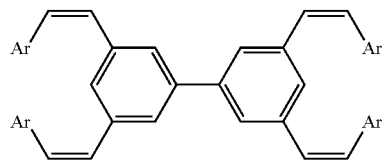

FIG. (C)

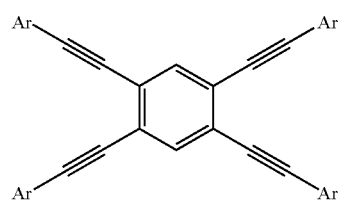

FIG. (D)

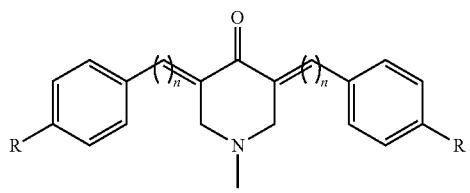

FIG. (E)

wherein each Ar is an aryl or substituted aryl; each R is alkyl; and n reflects the number of double bonds in the conjugated bridge and can be from 1 to 4.

In some embodiments, two or more photosensitive donors are included in the lens. The photosensitive donor(s) may be present in the lens in an amount of from about 0.05 to about 5 wt % of the lens.

In some embodiments, the chromophores may be selected from the group consisting of naphthalene sulfonyl chloride, quinolone sulfonyl chloride, and alpha-chloromethyl naphthalene. The chromophores may be present in the lens in an effective amount.

The first wavelength may be from about 1500 nm to about 350 nm. When the chromophore absorbs photons of different wavelengths, the second wavelength may also be from about 1500 nm to about 350 nm, but is different from the first wavelength.

In some other methods, a lens including a polymer matrix having photobleachable chromophores is used. A portion of the lens is exposed to non-visible radiation, causing photobleaching to occur in the exposed portion of the lens and changing the refractive index of the exposed portion of the lens, thereby altering the optical power of the lens. The lens may be a contact lens.

The non-visible radiation may be selected from gamma radiation, X-ray radiation, and ultraviolet radiation. In some embodiments, the non-visible radiation is provided by an excimer laser.

In some variations on this method, a portion of the lens is exposed instead to electromagnetic or charged particle radiation, causing photobleaching to occur in the exposed portion of the lens and changing the refractive index of the exposed portion of the lens, thereby altering the optical power of the lens. In some embodiments, the charged particle radiation is provided by an electron beam. The lens may be a contact lens.

In some other methods, a lens is provided that includes a single polymer matrix having crosslinkable pendant groups. The polymer matrix does not change significantly in volume when crosslinked. A portion of the lens is exposed to electromagnetic or charged particle radiation, causing crosslinking to occur in the exposed portion of the lens and changing the refractive index of the exposed portion of the lens, thereby altering the optical power of the lens.

The lens may be devoid of free monomers. In some embodiments, the charged particle radiation is provided by an electron beam.

Some methods comprise providing a lens including a polymer matrix containing a first chromophore and a second, different chromophore. The first chromophore acts as a photoinitiator or catalyst for bleaching the second chromophore, which causes the subsequent change in the refractive index of the lens. A portion of the lens is exposed to radiation, causing photobleaching to occur in the exposed portion of the lens and changing the refractive index of the exposed portion of the lens, thereby altering the optical power of the lens.

Two variations on this method are contemplated. First, the second chromophore is only bleached by the first chromophore, or in other words the second chromophore is not sensitive to the radiation. Second, the radiation causes the first chromophore to change from an inactive state to an active state. In the inactive state, the first chromophore does not bleach the second chromophore. In the active state, though, the first chromophore can act as a photoinitiator or catalyst for the second chromophore. The second chromophore is sensitive to both the radiation and to the first chromphore. In other words, bleaching of the second chromophore is faster than would be expected without the first chromophore.

The first chromophore may be selected from aromatic or aliphatic photoinitiators, or aromatic ketones such as benzophenone and thioxanthone. The first chromophore may be present in the lens in an amount of from about 0.05 to about 5 wt %. Exemplary first chromophores include Irgacure® molecules available from Ciba, such as 1-hydroxy-cyclohexyl-phenylketone (Irgacure® 184); 2-hydroxy-1-{4-[4-(2-hydroxy-2-methyl-propionyl)-benzyl]-phenyl}-2-methyl-propan-1-one (Irgacure® 127); 2-hydroxy-1-[4-(2-hydroxyethoxy)phenyl]-2-methyl-propanone (Irgacure® 2959); bis(2,4,6-trimethylbenzoyl)-phenylphosphineoxide (Irgacure® 819); 2-methyl-1-[4-(methylthio)phenyl]-2-morpholinopropan-1-one (Irgacure® 907); 2-benzyl-2-dimethylamino-1-(4-morpholinophenyl)-butan-1-one (Irgacure® 369); 2-dimethylamino-2-(4-methylbenzyl)-1-(4-morpholin-4-yl-phenyl)-butan-1-one (Irgacure® 379); and 2,2-dimethoxy-1,2-diphneylethan-1-one (Irgacure® 651).

In some embodiments the benzophenone is a compound of Formula (V):

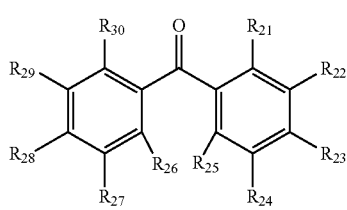

Formula (V)

wherein $R_{21}$-$R_{30}$ are independently selected from hydrogen, alkyl, substituted alkyl, aryl, substituted aryl, —COOH, —NO$_2$, halogen, amino, and substituted amino. In some embodiments, $R_{21}$-$R_{30}$ are hydrogen.

In some embodiments the thioxanthone is a compound of Formula (VI):

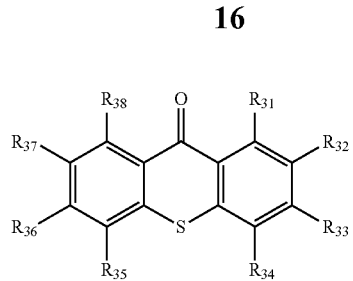

Formula (VI)

wherein $R_{31}$-$R_{38}$ are independently selected from hydrogen, alkyl, substituted alkyl, aryl, substituted aryl, —COOH, —NO$_2$, halogen, amino, and substituted amino. In some embodiments, $R_{31}$-$R_{38}$ are hydrogen.

The second chromophore may be selected from C.I. Solvent Blue 101; C.I. Reactive Blue 246; C.I. Pigment Violet 23; C.I. Vat Orange 1; C.I. Vat Brown 1; C.I. Vat Yellow 3; C.I. Vat Blue 6; C.I. Vat Green 1; C.I. Solvent Yellow 18; C.I. Vat Orange 5; C.I. Pigment Green 7; D&C Green No. 6; D&C Red No. 17; D&C Yellow No. 10; C.I. Reactive Black 5; C.I. Reactive Blue 21; C.I. Reactive Orange 78; C.I. Reactive Yellow 15; C.I. Reactive Blue 19; C.I. Reactive Blue 4; C.I. Reactive Red 11; C.I. Reactive Yellow 86; C.I. Reactive Blue 163; and C.I. Reactive Red 180. The second chromophore may be present in the lens in an amount of from about 0.5 to about 20 wt.

In still other methods, the lens comprises a polymer matrix having a chromophore. The lens is in proximity to a photoactivated bleaching catalyst. For example, the lens and the bleaching catalyst may be combined in a package, or the bleaching catalyst can be dispersed in the lens. Upon exposure to radiation, the bleaching catalyst causes photobleaching to occur in at least a portion of the lens, changing the refractive index of the exposed portion of the lens, thereby altering the optical power of the lens.

The photoactivated bleaching catalyst may be selected from peroxide-generating materials, singlet-oxide generating materials, and ozone-generating materials. Exemplary peroxide-generating materials are known in the art. Exemplary singlet-oxide generating materials include are known in the art. Exemplary ozone-generating materials include are known in the art.

Finally, it is contemplated that the lens can include a polymer matrix having photobleachable chromophores; and initiating a reaction to photobleach the chromophores. The reaction is selected from the group consisting of an oxidation or reduction reaction, a catalytic acid or base reaction, a dimerization reaction, a molecular rearrangement reaction, a free radical propagation reaction, a free radical non-propagation reaction, a reaction changing the number of unsaturation sites, a charge transfer reaction, and a chromophore modification reaction.

The concept of controlling the refractive index of a material without changing its shape allows a lens to be fabricated into a uniform sheet of polymer that has been doped with suitable chromophores. This allows the creation of a Fresnel lens from a sheet of material that is smooth and much easier to fabricate and clean. This lens could be used in photovoltaic applications, where cleaning of mirrors and photovoltaic surfaces is the largest portion of the operations budget. Alternately a lens could be created in a panel or window to allow for control of light passing through the window or panel. This could be used for architectural or design purposes, or alternately may have applications in controlling light passing through the panel.

Use of the various methods described above are also specifically contemplated for use with intraocular lenses and with contact lenses. Contact lenses are generally made from biocompatible polymers which do not damage the ocular tissue and ocular fluid during the time of contact. In this regard, it is known that the contact lens must allow oxygen to reach the cornea. Extended periods of oxygen deprivation causes the undesirable growth of blood vessels in the cornea. "Soft" contact lenses conform closely to the shape of the eye, so oxygen cannot easily circumvent the lens. Thus, soft contact lenses must allow oxygen to diffuse through the lens to reach the cornea.

Another ophthalmic compatibility requirement for soft contact lenses is that the lens must not strongly adhere to the eye. The consumer must be able to easily remove the lens from the eye for disinfecting, cleaning, or disposal. However, the lens must also be able to move on the eye in order to encourage tear flow between the lens and the eye. Tear flow between the lens and eye allows for debris, such as foreign particulates or dead epithelial cells, to be swept from beneath the lens and, ultimately, out of the tear fluid. Thus, a contact lens must not adhere to the eye so strongly that adequate movement of the lens on the eye is inhibited.

Suitable materials for contact lenses are well known in the art. For example, polymers and copolymers based on 2-hydroxyethyl methacrylate (HEMA) are known, as are siloxane-containing polymers that have high oxygen permeability, as well as silicone hydrogels. Any suitable material can be used for the polymer matrix of a contact lens to which the methods described herein can be applied.

Aspects of the present disclosure may be further understood by referring to the following examples. The examples are merely for further describing various aspects of the devices and methods of the present disclosure and are not intended to be limiting embodiments thereof.

EXAMPLES

Experimental measurements were performed to verify that the refractive index changed upon crosslinking and without the presence of free monomer. The experiments also showed that the refractive index change was controllable, reproducible, and adjustable.

A series of experiments were also performed to verify the amount of change in the refractive index possible with photobleaching, and also that photobleaching could occur in an aqueous environment.

Example 1

A solution of 37.5% SARTOMER CN990, 59.4% SARTOMER SR344 and 3.1% DAROCUR 4265 was created (composition was based on weight fraction of the components). SARTOMER CN990 is a siliconized urethane acrylate oligomer. SARTOMER SR344 is a polyethylene glycol diacrylate having a molecular weight of 508. DAROCUR 4265 is a photoinitiator mixture of 50 weight percent diphenyl (2,4,6-trimethylbenzoyl) phosphine oxide and 50 weight percent 2-hydroxy-2-methyl-1-phenyl-1-propanone. DAROCUR 4265 has absorption peaks at 240, 272, and 380 nm in methanol.

The refractive index of the solution was measured to be 1.4717. The solution was then cast onto a slide and exposed to 10 seconds of UV light from a lamp source. The refractive index of the film was then measured using a Metricon Model 2010 Prism Coupler, and was determined to be 1.4747. Additional UV exposure of 5 seconds gave a refractive index of n=1.4852. Further UV exposure of 15 seconds gave a refractive index of n=1.4868. In other words, as the amount of UV exposure increased, the amount of crosslinking increased and thus the refractive index increased.

Example 2

The solution of Example 1 was again created, except the DAROCUR 4265 was replaced with IRGACURE 2959, which is sensitive to 254 nm UV. The solution was cast onto a plate and exposed to UV light. After 2 seconds exposure, the refractive index was measured with the prism coupler and found to be n=1.4668, with the film not being fully cured in the center. An additional 5 second UV exposure led to the refractive index being measured as n=1.485.

Example 3

Figure 12:
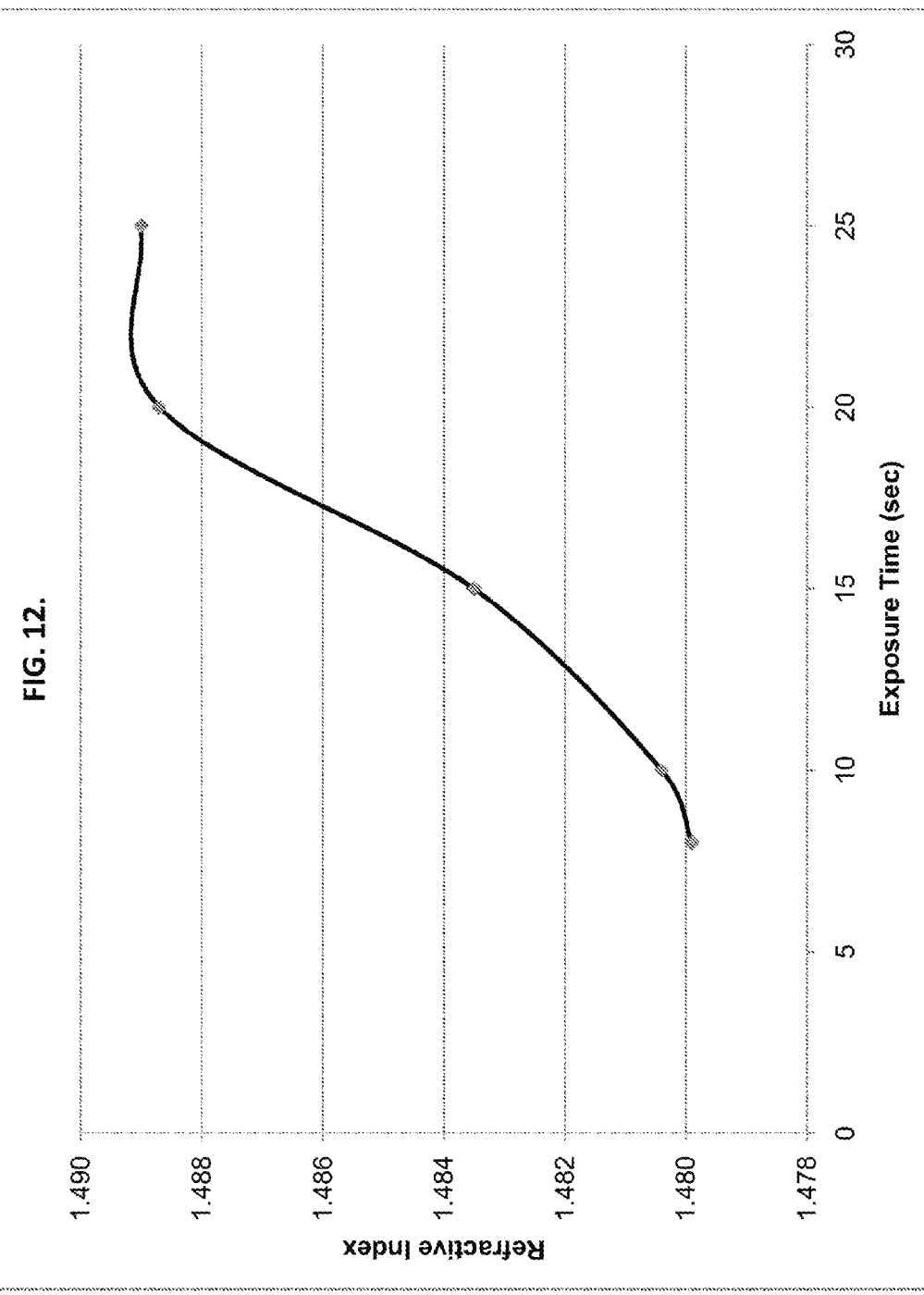
FIG. 12 is a graph showing the refractive index of a lens as a function of the amount of time the lens was exposed to UV radiation.

A third experiment was performed to better evaluate the exposure-dependence of the refractive index. A solution similar to that of Example 1 was prepared and cast onto a slide. The film then underwent several cycles of UV exposure and refractive index measurement. The results are shown in FIG. 12. Below 8 seconds exposure, the film was not fully set. The data is also summarized in Table 1.

TABLE 1

| Time (sec) | Refractive Index |
|---|---|
| 8 | 1.4799 |
| 10 | 1.4804 |
| 15 | 1.4835 |
| 20 | 1.4887 |
| 25 | 1.489 |

The results indicated that the refractive index could be changed by a range of about 0.01 after exposure of about 25 seconds. This value of index change was selected as providing approximately a 10% change in lens power (as shown in FIG. 2).

Example 4

A solution of VC60 in polymethylmethacrylate (PMMA) was cast as a film and dried at 80° C. for 10 minutes. The refractive index of the film was 1.4909. The film was then exposed to 254 nm radiation for 1 minute. The refractive index was then measured to be 1.5016. After further exposure (30 minutes total) the refractive index was 1.5036. Absorbance measurements showed ~50% decrease in absorbance due to the chromophore.

Example 5

A solution of EC24 in PMMA was cast as a film and dried at 80° C. for 10 minutes. The refractive index of the film was measured as n=1.5014. The film was then exposed to 254 nm radiation for 30 minutes. The refractive index was then measured as n=1.4924.

Example 6

EC24 was then diffused into an ACUVUE lens (Johnson & Johnson Vision Care, Inc.). The lens was partially masked, then exposed to 254 nm UV light for 30 minutes. The chromophore bleached, but over time the demarcation line between the masked and unmasked portions of the lens blurred. This may be attributable to migration of the chromophore in the lens.

The experiment was then repeated by diffusing EC24 into two separate ACUVUE lenses. The first lens was kept as a control, and exhibited very uniform red color, consistent with an absorption maximum near 510 nm for EC24 in the lens. The second lens was exposed to the UV light for 30 minutes. At the end of this exposure, the second lens exhibited no color and was completely transparent.

Example 7

Figure 13:
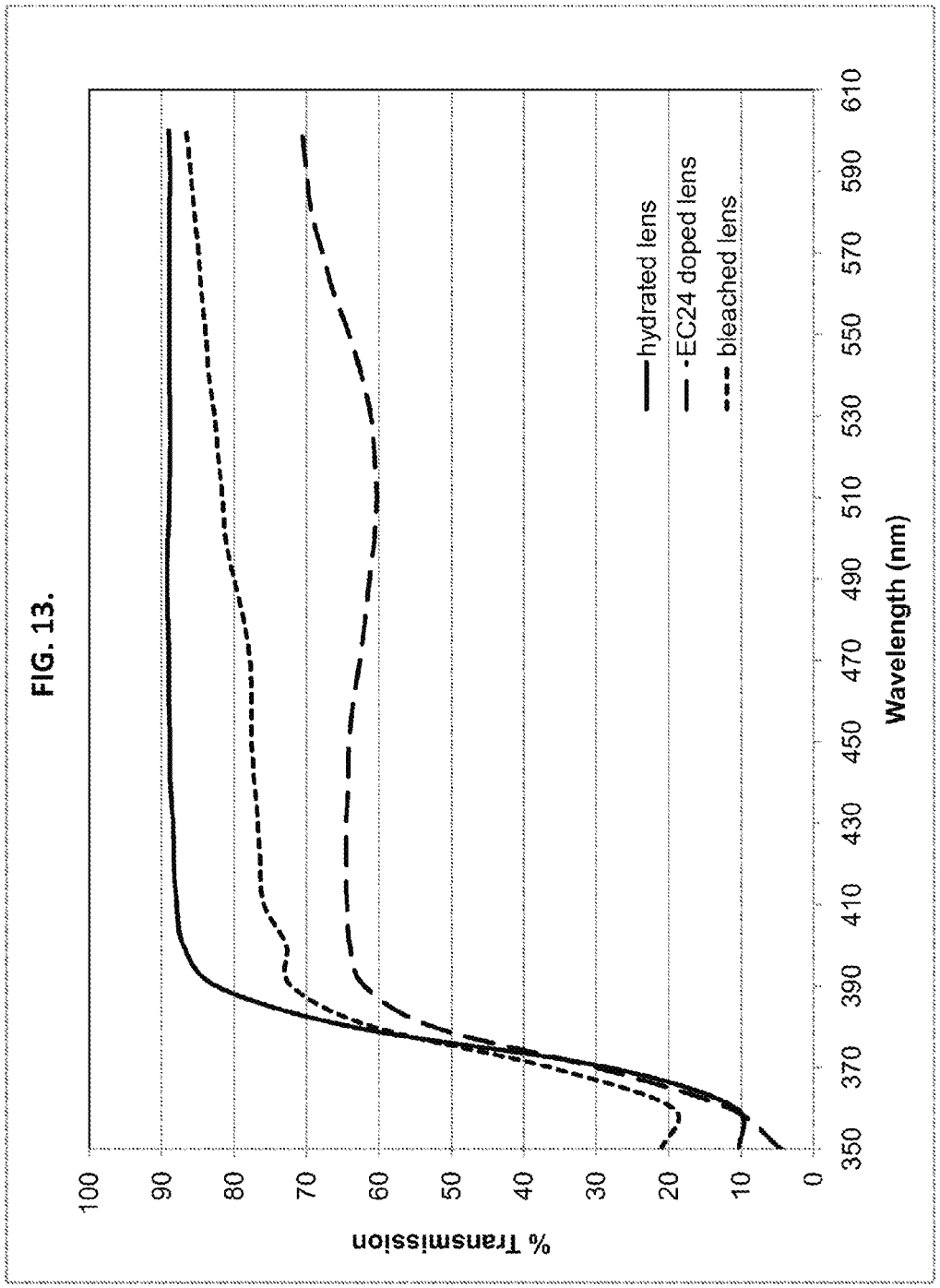
FIG. 13 is a graph showing the transmission spectrum of a contact lens before application of a chromophore, before bleaching, and after bleaching.

The transmission spectra of an ACUVUE lens was measured. EC24 was then diffused into the lens, and the transmission spectrum was measured again. Finally, the lens was bleached and the transmission spectrum was measured a third time. The results are shown in FIG. 13 and Table 2.

TABLE 2

| Wavelength (nm) | % T hydrated lens | % T EC24 doped lens | % T bleached lens |
| --- | --- | --- | --- |
| 350 | 10.3 | 4.5 | 21 |
| 360 | 10.7 | 11.7 | 19.4 |
| 370 | 28.4 | 30.1 | 36.4 |
| 380 | 63.9 | 52.6 | 60.9 |
| 390 | 82.5 | 62 | 72.1 |
| 400 | 87 | 64 | 72.8 |
| 410 | 87.9 | 64.4 | 75.9 |
| 420 | 88.3 | 64.5 | 76.4 |
| 430 | 88.4 | 64.5 | 76.7 |
| 440 | 88.8 | 64.2 | 77.2 |
| 450 | 88.8 | 64.1 | 77.6 |
| 460 | 89 | 63.5 | 77.6 |
| 470 | 89 | 62.6 | 77.8 |
| 480 | 89.1 | 61.9 | 78.7 |
| 490 | 89.2 | 61.3 | 80 |
| 500 | 89.1 | 60.6 | 81.2 |
| 510 | 88.9 | 60.3 | 81.6 |
| 520 | 88.8 | 60.6 | 82.2 |
| 530 | 88.8 | 61.1 | 82.7 |
| 540 | 88.9 | 62.4 | 83.5 |
| 550 | 88.9 | 64.1 | 83.9 |
| 560 | 88.9 | 66.2 | 84.5 |
| 570 | 88.9 | 67.8 | 84.9 |
| 580 | 88.9 | 69.3 | 85.5 |
| 590 | 88.8 | 70 | 86 |
| 600 | 89 | 70.6 | 86.6 |

Note that the EC24 doped lens shows a transmission minimum close to 510 nm, while the absorption maximum of EC24 in dioxane was measured to be 503 nm. This indicates that the EC24 is present in the doped lens. The photobleached lens has weaker absorption and no longer has the absorption at 510 nm, indicating that the photobleaching process has altered the chemistry of EC24.

The devices and methods of the present disclosure have been described with reference to exemplary embodiments. Obviously, modifications and alterations will occur to others upon reading and understanding the preceding detailed description. It is intended that the exemplary embodiments be construed as including all such modifications and alterations insofar as they come within the scope of the appended claims or the equivalents thereof.

The invention claimed is:

1. A method of altering the optical power of a lens, comprising:
   providing a lens comprising:
      a polymer matrix having photobleachable chromophores; and
      a photosensitive donor lacking photoinitiating groups and responsive to a first selective wavelength of energy for generating primary excited state donor molecules which are not responsive to said first selective wavelength, but are responsive to sequentially applied second selective wavelengths of energy for generating secondary higher energy level excited state donor molecules;
   the chromophores having a lowest primary excited state greater than the primary excited state of the photosensitive donor, the secondary higher energy level excited state of the photosensitive donor molecules being greater than the lowest primary excited state of the chromophores; and
   exposing a portion of the lens to radiation at the first selective wavelength to generate primary excited state donor molecules; and
   exposing the exposed portion of the lens to radiation of the second selective wavelength to generate secondary higher energy level excited state donor molecules, causing photobleaching to occur in the exposed portion of the lens and changing the refractive index of the exposed portion of the lens, thereby altering the optical power of the lens;
   wherein the photosensitive donor is selected from the group consisting of Formulas (A)-(E):

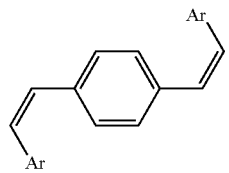

Formula (A)

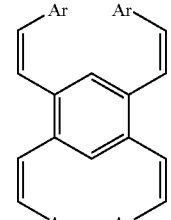

Formula (B)

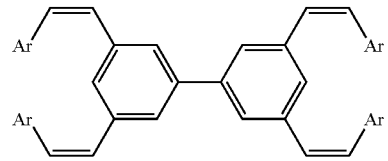

Formula (C)

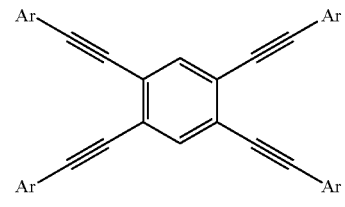

Formula (D)

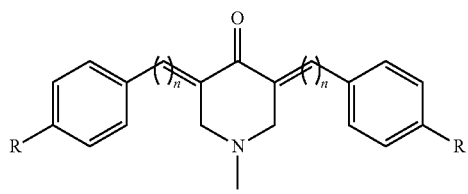

Formula (E)

wherein each Ar is an aryl or substituted aryl; each R is alkyl; and n reflects the number of double bonds in the conjugated bridge and can be from 1 to 4.

2. The method of claim 1, wherein the lens is a contact lens.

3. The method of claim 1, wherein the chromophores are selected from the group consisting of naphthalene sulfonyl chloride, quinolone sulfonyl chloride, and alpha-chloromethyl naphthalene.

4. The method of claim 1, wherein the first and second wavelengths are different.

5. A method of altering the optical power of a lens, comprising:
providing a lens comprising a polymer matrix containing a first chromophore and a second chromophore; and
exposing a portion of the lens to radiation, causing photobleaching to occur in the exposed portion of the lens and changing the refractive index of the exposed portion of the lens, thereby altering the optical power of the lens;
wherein the first chromophore is sensitive to the radiation and is a photoinitiator or catalyst for bleaching the second chromophore;
wherein the first chromophore is an aromatic ketone; and
wherein the second chromophore is selected from the group consisting of C.I. Solvent Blue 101; C.I. Reactive Blue 246; C.I. Pigment Violet 23; C.I. Vat Orange 1; C.I. Vat Brown 1; C.I. Vat Yellow 3; C.I. Vat Blue 6; C.I. Vat Green 1; C.I. Solvent Yellow 18; C.I. Vat Orange 5; C.I. Pigment Green 7; D&C Green No. 6; D&C Red No., 17; D&C Yellow No. 10; C.I. Reactive Black 5; C.I. Reactive Blue 21; C.I. Reactive Orange 78; C.I. Reactive Yellow 15; C.I. Reactive Blue 19; C.I. Reactive Blue 4; C.I. Reactive Red 11; C.I. Reactive Yellow 86; C.I. Reactive Blue 163; and C.I. Reactive Red 180.

6. The method of claim 5, wherein the second chromophore is not sensitive to the radiation but is sensitive to the first chromophore.

7. The method of claim 5, wherein the first chromophore is transformed from an inactive state to an active state by the exposure to the radiation.

8. The method of claim 5, wherein the first chromophore is present in an amount of from about 0.05 to about 5 wt %; and wherein the second chromophore is present in an amount of from about 0.5 to about 20 wt %.

* * * * *